US010201518B2

(12) United States Patent
Sun et al.

(10) Patent No.: US 10,201,518 B2
(45) Date of Patent: Feb. 12, 2019

(54) BISMUTH(III) COMPOUNDS AND METHODS THEREOF

(71) Applicant: THE UNIVERSITY OF HONG KONG, Hong Kong (CN)

(72) Inventors: Hongzhe Sun, Ap Lei Chau (HK);
Richard Yi Tsun Kao, Kowloon (HK);
Runming Wang, Hong Kong (HK); Tsz Pui Lai, New Territories (HK);
Hongmin Zhang, Aberdeen (HK);
Hongyan Li, Ap Lei Chau (HK)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 15/278,916

(22) Filed: Sep. 28, 2016

(65) Prior Publication Data
US 2018/0085335 A1   Mar. 29, 2018

(51) Int. Cl.
*A61K 31/28*   (2006.01)
*A61K 31/407*   (2006.01)

(52) U.S. Cl.
CPC ............ *A61K 31/28* (2013.01); *A61K 31/407* (2013.01)

(58) Field of Classification Search
CPC ..................................................... A61K 31/28
USPC .................................................... 514/210.13
See application file for complete search history.

(56) References Cited

U.S. PATENT DOCUMENTS

| 5,674,858 | A | 10/1997 | Mccolm et al. |
| 9,028,878 | B2 | 5/2015 | Baker |
| 2012/0122768 | A1 | 5/2012 | Onsoyen et al. |
| 2012/0329770 | A1 | 12/2012 | Dmitrienko et al. |
| 2012/0329842 | A1 | 12/2012 | Song et al. |
| 2013/0023512 | A1 | 1/2013 | Chaudhary |
| 2014/0194386 | A1 | 7/2014 | Burns et al. |
| 2014/0315861 | A1 | 10/2014 | Shoichet et al. |
| 2015/0031767 | A1 | 1/2015 | Leivers et al. |

FOREIGN PATENT DOCUMENTS

| CN | 200610045806 | 2/2006 |
| CN | 200810097687 | 5/2008 |
| CN | ZL200910010693 | 3/2009 |
| CN | 201110258952 | 9/2011 |
| EP | 19890203250 | 12/1989 |
| WO | WO1996008259 | 3/1996 |
| WO | WO2008035085 | 3/2008 |

OTHER PUBLICATIONS

Toney et al. Current Opinion in Investigational Drugs, (2004), 5(8), p. 1-4.*

Galkin et al. Polish Journal of Microbiology (2015), 64(2), p. 101-106.*
Wright, G. D.; Sutherland, A. D., New strategies for combating multidrug-resistant bacteria, Trends Molecular Medicine 2007, vol. 13, No. 6 pp. 260-267.
Fisher, J. F.; Meroueh, S. O., Mobashery, S., Bacterial Resistance to β-Lactam Antibiotics: Compelling Opportunism, Compelling Opportunity, Chemical Reviews 2005, 105, pp. 395-424.
Medeiros, A. A., Evolution and Dissemination of β-Lactamases Accelerated by Generations of β-Lactam Antibiotics, Clinical Infectious Diseases 1997, 24, p. S19-45.
Walsh, T. R.; Toleman, M. A.; Poirel, L.; Nordmann, P., Metallo-β-Lactamases: the quiet before the Storm?, Clinical Microbiology Reviews 2005, vol. 18, No. 2, pp. 306-325.
Feng, H.; Ding, J.; Zhu, D.; Liu, X.; Xu, X.; Zhang, Y.; Zang, S.; Wang, D.-C.; Liu, Structural and Mechanistic Insights into NDM-1 Catalyzed Hydrolysis of Cephalosporins, W. Journal of the American Chemical Society 2014, 136, pp. 14694-14697.
Tripathi, R.; Nair, N. N., Mechanism of Meropenem Hydrolysis by New Delhi Metallo β-Lactamase, ACS Catalysis 2015, 5, pp. 2577-2586.
Cornaglia, G.; Giamarellou, H.; Rossolini, G. M., Metallo-β-lactamases: a last frontier for β-lactams?, The Lancet Infectious Diseases, May 2011, vol. 11, pp. 381-393.
Munoz-Price, L. S.; Poirel, L.; Bonomo, R. A.; Schwaber, M. J.; Daikos, G. L.; Cormican, M.; Cornaglia, G.; Garau, J.; Gniadkowski, M.; Hayden, M. K.; Kumarasamy, K.; Livermore, D. M.; Maya, J. J.; Nordmann, P.; Patel, J. B.; Paterson, D. L.; Pitout, J.; Villegas, M. V.; Wang, H.; Woodford, N.; Quinn, J. P., Clinical epidemiology of the global expansion of Klebsiella pneumoniae carbapenemases, The Lancet Infectious Diseases, Sep. 2013, 13(9), pp. 785-796.
Lippmann, N.; Lübbert, C.; Kaiser, T.; Kaisers, U. X.; Rodloff, A. C., Clinical epidemiology of Klebsiella pneumoniae Carbapenemases, The Lancet Infectious Diseases, 2014, 14, 271.
Nordmann, P.; Cuzon, G.; Naas, T., The real threat of Klebsiella pneumoniae carbapenemaseproducing Bacteria, The Lancet Infectious Diseases, Apr. 2009, vol. 9, pp. 228-236.
Poirel, L.; Nordmann, P., Carbapenem resistance in Acinetobacter baumannii: mechanisms and Epidemiology, Clinical Microbiology and Infection 2006, 12, pp. 826-836.
Queenan, A. M.; Bush, K., Carbapenemases: the Versatile β-Lactamases, Clinical Microbiology Reviews, Jul. 2007, vol. 20, No. 3, pp. 440-458.
Woodford, N.; Turton, J. F.; Livermore, D. M., Multiresistant Gram-negative bacteria: the role of high-riskclones in the dissemination of antibiotic resistance, FEMS Microbiology Reviews 2011, 35, pp. 736-755.

(Continued)

*Primary Examiner* — Yong L Chu
(74) *Attorney, Agent, or Firm* — Leason Ellis LLP

(57) ABSTRACT

The present disclosure relates to a pharmaceutical composition comprising: (a) β-lactam antibiotics and (b) a metallo-β-lactamases (MBLs) inhibitor. The inhibitor relates to Bi(III) compounds or the pharmaceutically acceptable salts thereof. The present patent also provides methods of making Bi(III) compounds or the pharmaceutically acceptable salts thereof. Also provided is a method for treating MBLs-producing bacterial infection using a metal replacement mechanism.

11 Claims, 15 Drawing Sheets

(56) References Cited

OTHER PUBLICATIONS

Kumarasamy, K. K.; Toleman, M. A.; Walsh, T. R.; Bagaria, J.; Butt, F.; Balakrishnan, R.; Chaudhary, U.; Doumith, M.; Giske, C. G.; Irfan, S.; Krishnan, P.; Kumar, A. V.; Maharjan, S.; Mushtaq, S.; Noorie, T.; Paterson, D. L.; Pearson, A.; Perry, C.; Pike, R.; Rao, B.; Ray, U.; Sarma, J. B.; Sharma, M.; Sheridan, E.; Thirunarayan, M. A.; Turton, J.; Upadhyay, S.; Warner, M.; Welfare, W.; Livermore, D. M.; Woodford, N., Emergence of a new antibiotic resistance mechanism in India, Pakistan, and the UK: a molecular, biological, and epidemiological study, The Lancet Infectious Diseases, Sep. 2010, vol. 10, pp. 597-602.
Nordmann, P.; Naas, T.; Poirel, L., Global Spread of Carbapenemase producing Enterobacteriaceae, Emerging Infectious Diseases, Oct. 2011, vol. 17, No. 10, pp. 1791-1798.
Borgia, S.; Lastovetska, O.; Richardson, D.; Eshaghi, A.; Xiong, J.; Chung, C.; Baqi, M.; McGeer, A.; Ricci, G.; Sawicki, R.; Pantelidis, R.; Low, D. E.; Patel, S. N.; Melano, R. G., Outbreak of Carbapenem-Resistant Enterobacteriaceae Containing $bla_{NDM-1}$, Clinical Infectious Diseases, Dec. 2012, 55, pp. e109-e117.
Cantön, R.; Akóva, M.; Carmeli, Y.; Giske, C. G.; Glupczynski, Y.; Gniadkowski, M.; Livermore, D. M.; Miriagou, V.; Naas, T.; Rossolini, G. M.; Samuelsen, Ø.; Seifert, H.; Woodford, N.; Nordmann, P., Rapid evolution and spread of carbapenemases among Enterobacteriaceae in Europe, Clinical Microbiology and Infection 2012, 18, pp. 413-431.
Shahcheraghi, F.; Nobari, S.; Rahmati Ghezelgeh, F.; Nasiri, S.; Owlia, P.; Nikbin, V. S.; Imani Fooladi, A. A., First Report of New Delhi Metallo-Beta-Lactamase-1-Producing Klebsiella pneumoniae in Iran, Microbial Drug Resistance 2012, 19, 30.
Ho, H. J.; Toh, C. Y.; Ang, B.; Krishnan, P.; Lin, R. T. P.; La, M.-V.; Chow, A., Outbreak of New Delhi metallo-b-lactamase-1eproducing Enterobacter cloacae in an acute care hospital general ward in Singapore, American Journal of Infection Control 2016, 44, pp. 177-182.
Saliba, V.; Washer, P.; Pett, P.; Kakkar, M.; Abbas, S.; Raghuvanshi, B.; McKee, M., J Public Health Pol 2016, vol. 37, I, pp. 1-19.
Yong, D.; Toleman, M. A.; Giske, C. G.; Cho, H. S.; Sundman, K.; Lee, K.; Walsh, T. R., Characterization of a New Metallo-b-Lactamase Gene, blaNDM-1, and a Novel Erythromycin Esterase Gene Carried on a Unique Genetic Structure in Klebsiella pneumoniae Sequence Type 14 from India, Antimicrobial Agents and Chemotherapy 2009, vol. 53, No. 12, pp. 5046-5054.
Chen, Y.; Zhou, Z.; Jiang, Y.; Yu, Y., Emergence of NDM-1-producing Acinetobacter baumannii in China, Journal of Antimicrobial Chemotherapy 2011, 66, pp. 1255-1259.
Ho, P. L.; Lo, W. U.; Yeung, M. K.; Lin, C. H.; Chow, K. H.; Ang, I.; Tong, A. H. Y.; Bao, J. Y.-J.; Lok, S.; Lo, J. Y. C., Complete Sequencing of pNDM-HK Encoding NDM-1 Carbapenemase from a Multidrug-Resistant *Escherichia coli* Strain Isolated in Hong Kong PLoS ONE, Mar. 2011, vol. 6, Issue 3, e17989.
Gupta, N.; Limbago, B. M.; Patel, J. B.; Kallen, A., Carbapenem-Resistant Enterobacteriaceae: Epidemiology and Prevention, J. Clinical Infectious Diseases 2011, 53, pp. 60-67.
Reading, C.; Cole, M., Clavulanic Acid: a Beta-Lactamase-Inhibiting Beta-Lactam from Streptomyces clavuligerus, Antimicrobial Agents and Chemotherapy, May 1977, vol. 11, No. 5, pp. 852-857.

Ehmann, D. E.; Jahić, H.; Ross, P. L.; Gu, R.-F.; Hu, J.; Kern, G.; Walkup, G. K.; Fisher, S. L., Avibactam is a covalent, reversible, non-β-lactam β-lactamase inhibitor Proceedings of the National Academy of Sciences, Jul. 17, 2012, vol. 109, No. 29, pp. 11663-11668.
Gardiner, B. J.; Golan, Y., Ceftazidime-avibactam (CTZ-AVI) as a treatment for hospitalized adult patients with complicated intra-abdominal infections, Expert Rev Anti Infect Ther 2016, vol. 14, No. 5, pp. 451-463.
King, A. M.; Reid-Yu, S. A.; Wang, W.; King, D. T.; De Pascale, G.; Strynadka, N. C.; Walsh, T. R.; Coombes, B. K.; Wright, G. D., AMA overcomes antibiotic resistance by NDM and VIM metallo-β-lactamases, Nature, Jun. 26, 2014, 510(7506), pp. 503-506.
Brem, J.; van Berkel, S. S.; Aik, W.; Rydzik, A. M.; Avison, M. B.; Pettinati, I.; Umland, K.-D.; Kawamura, A.; Spencer, J.; Claridge, T. D. W.; McDonough, M. A.; Schofield, C., Rhodanine hydrolysis leads to potent thioenolate mediated metallo-β-lactamase inhibition, J. Nat Chem, Dec. 2014, vol. 6, pp. 1084-1090.
Klingler, F.-M.; Wichelhaus, T. A.; Frank, D.; Cuesta-Bernal, J.; El-Delik, J.; Müller, H. F.; Sjuts, H.; Göttig, S.; Koenigs, A.; Pos, K. M.; Pogoryelov, D.; Proschak, E., Approved Drugs Containing Thiols as Inhibitors of Metallo-β-lactamases: Strategy to Combat Multidrug-Resistant Bacteria, Journal of Medicinal Chemistry 2015, 58, pp. 3626-3630.
Brem, J. et al., Rhodanine hydrolysis leads to potent thioenolate mediated metallo-β-lactamase inhibition, Rhodanine hydrolysis leads to potent thioenolate mediated metallo-β-lactamase inhibition, Nature Chem., Dec. 2014, vol. 6, pp. 1084-1090.
Falconer, S. B. et al., Zinc chelation by a small-molecule adjuvant potentiates meropenem activity in vivo against NDM-1-producing Klebsiella pneumoniae, ACS Infectious Diseases, 2015, 1, pp. 533-543.
Gonzalez, M. M. et al., Bisthiazolidines: A Substrate-mimicking scaffold as an inhibitor of the NDM-1 carbapenemase, ACS Infectous Diseases, (2015), 1, pp. 544-554.
Tsang, W. Y. et al., The inhibition of metallo-lactamase by thioxo-cephalosporin derivatives, Bioorganic & Medicinal chemistry Letters 14 (2004), pp. 1737-1739.
Dirk L. Van Caekenberghe, et al., In vitro synergistic activity between bismuth subcitrate and various antimicrobial agents against Campylobacter pyloridis (C. pylori)., Antimicrob Agents Chemother. Sep. 1987;31(9): pp. 1429-1430.
T O'Riordan, et al., Adjuvant antibiotic therapy in duodenal ulcers treated with colloidal bismuth subcitrate., Gut. Sep. 1990;31(9): pp. 999-1002.
P.D. Midolo, et al., In vitro synergy between ranitidine bismuth citrate and tetracycline or clarithromycin against resistant strains of Helicobacter pylori., Eur J Clin Microbiol Infect Dis. Nov. 1999;18(11): pp. 832-834.
Francis Mégraud, et al., Ranitidine Bismuth Citrate Can Help to Overcome Helicobacter pylori Resistance to Clarithromycin In Vivo., Helicobacter. Dec. 2000;5(4):222-6.
Elizabeth A. Marcus, et al., Colloidal bismuth subcitrate impedes proton entry into Helicobacter pylori and increase the efficacy of growth-dependent antibiotics, Aliment Pharmacol Ther. Oct. 2015;42(7): pp. 922-933.

\* cited by examiner

BISMUTH(III) COMPOUNDS AND METHODS THEREOF

1. INTRODUCTION

Disclosed herein is a pharmaceutical composition comprising: (a) β-lactam antibiotics and (b) a metallo-β-lactamases (MBLs) inhibitor. In one embodiment, the inhibitor relates to Bi(III) compounds or the pharmaceutically acceptable salts thereof. More specifically, the pharmaceutical composition comprises effective amounts of: (a) a β-lactam antibiotic; and (b) Bi(III) compounds or the pharmaceutically acceptable salts thereof. Also provided is a method for preventing or treating MBLs-producing bacterial infection. The present disclosure also provides methods of making the composition that comprises the β-lactam antibiotic and the MBLs inhibitor. The disclosure also relates to the modulation of MBL activity by Bi(III) compounds. The MBLs inhibitor inhibits MBLs using a metal replacement mechanism. In certain embodiments, the disclosed composition comprises a compound that is a broad-spectrum anti-bacterial agent for treating topical, local and/or systemic bacterial infections. In certain embodiments, the disclosed compound is used in the treatment of infections caused by MBL-producing bacterial pathogens. Provided herein is a medical device comprising a coating comprising the compound disclosed herein. Provided herein is a method of making a medical device comprising a coating comprising the compound disclosed herein. Provided herein is a method of making an anti-biofilm surface.

2. BACKGROUND

Beta-lactam antibiotics are the most widely used antibacterial drugs in the treatment of bacterial infections. As a fierce fight back, bacteria produce enzymes called β-lactamases, which break down the β-lactams, leading to a broad-spectrum resistance to this class of antibiotics. The emergence and spreading of β-lactamases constitutes an enormous threat to public health globally.[1-3]

Based on the unique enzymatic mechanisms, β-lactamases can be functionally classified to two major types, i.e. serine-β-lactamases (SBLs) and metallo-β-lactamases (MBLs) with the former employing a serine as a nucleophile and the latter using zinc ions to breakdown β-lactam ring.[4] MBLs are considered as the more injurious β-lactamases conferring a broad-spectrum of resistance to β-lactam antibiotics due to their unique enzymatic mechanism.[5-7] This is largely due to the followings: (1) resistant determinants of MBLs are often encoded on mobile genetic elements and could easily spread among/across a variety of bacterial species by horizontal gene transfer. The predominant MBLs producers, Enterobacteriaceae including *Escherichia* spp., *Klebsiella* spp., *Pseudomonas* spp., *Acinetobacter* spp. and *Enterococcus*. spps., could be easily found in community and even health-care context, and spread among people by hand carriage, food and water.[8-11] (2) MBLs have strong β-lactamase activity and are able to hydrolyze or inactivate the most commonly used β-lactam antibiotics, such as cephalosporins and carbapenems. Furthermore most MBLs producing enterobacterial strains are able to co-express other types of resistance genes including those encoding other β-lactamases (AmpC, ESBL, OXA-48 and KPC) and resistance determinants for other antibiotics including fluoroquinolones (qnrA6 and qnrB1), aminoglycosides (armA, rmtA and rmtC), acrolides (ereC), rifampicin (arr-2) and sulfonamide (sul-2).[4,12,13] The latest example of MBLs is New Delhi metallo-β lactamase-1 ("NDM-1"). In 2009, a Swedish patient was firstly reported to be infected by NDM-1 producing *Klebsiella pneumoniae* with resistance to multiple antibiotics including all carbapenems upon the return from India.[9] Ever since, NDM-1 has been spread to all inhabited continents wherein Indian subcontinent and China emerge as the two biggest reservoirs, and therefore NDM-s is often regarded as the notorious "superbug" in mass medium.[14-23] However, there appears no effective treatment for the infection caused by NDM-1.

There is a lack of inhibitor specifically targeting MBLs available clinically up to date. MBLs are considered more menacing than SBLs owing to the following two aspects: (1) the architectures of active sites of MBLs vary greatly among microorganisms. Thus it remains to be a great challenge to design an inhibitor against all MBLs among different bacteria. (2) Unlike SBLs, MBLs have no or few stable reaction intermediates, which immensely increase the difficulty in copying the inhibition mode of SBLs inhibitor, such as clavulanic acid.[7,12]

Till now, considerable efforts have been made for the development of MBL inhibitors. A representative MBL inhibitor is Aspergillomarasmine A (AMA) reported in Nature, 2014, which is effective against MBLs (mainly for NDM-1 and VIM-2) among a variety of gram-negative bacteria and exerts good in vivo efficacy against *K. pneumonia* (NDM$^+$).[28] Another example is a rhodanine-derived thioenolate showing a potent broad-spectrum activity against MBLs. The thioenolate is found to bind VIM-2 via di-zinc chelation by crystallography.[29] Since then, quite a few MBL inhibitors began to emerge and make progress in this area, but their in vivo efficacies have not been proved yet. Above instances mirror the conventional way to deal with MBLs, i.e. designing inhibitors which are able to coordinate to or chelate Zn(II) in the active sites, such as carboxylic acids and thiol-containing compounds. But such a strategy usually suffer from relatively poor selectivity and low efficacy and is unlikely to develop a wide-spectrum of MBL inhibitors, not to mention the hidden worry of the generation of resistance to those organic inhibitors by microorganisms. Furthermore, though some FDA-approved drugs, such as DL-captopril, glutathione and 2,3-dimercaprol,[30] have been used in the studies, no clinically available MBL inhibitor has been approved yet. Therefore, there appears to be lack of developments of the relevant MBLs inhibitors.

3. SUMMARY

Provided herein is a composition comprising: (a) β-lactam antibiotics; and (b) metallo-β-lactamases (MBLs) inhibitor. The inhibitor relates to Bi(III) compounds or pharmaceutically acceptable salts thereof, that modulate the activity of MBLs via an unprecedented metal replacement mechanism. In addition, MBLs inhibitors are efficient β-lactam antibiotic partners for the treatment of infection caused by MBL-producing bacterial pathogens. In certain embodiments, infections that are treated by the disclosed composition are caused by bacteria that are resistant to β-lactam antibiotics. In certain embodiments, the β-lactam antibiotics have the following core structure:

The β-lactam core structures. (A) A penam. (B) A carbapenam. (C) An oxapenam. (D) A penem. (E) A carbapenem. (F) A monobactam. (G) A cephem. (H) A carbacephem. (I) An oxacephem In certain embodiments, the β-lactam antibiotics are penicillins, cephalosporins, and carbapenems. In certain embodiments, the bacteria are gram-negative. In certain embodiments, the bacteria produce metallo-β-lactamases ("MBL"s). In certain embodiments, the MBLs are imipenemase ("IMP"), Verona integrin-encoded metallo-β-lactamase ("VIM") and New Delhi metallo-beta-lactamase ("NDM").

Provided herein are methods of preparing Bi(III) compounds by either repositioning of Bi(III) drugs or coordinating Bi(III) to N, O, or S containing ligands. Examples of the ligands of Bi (III) compounds include, but are not limited to,

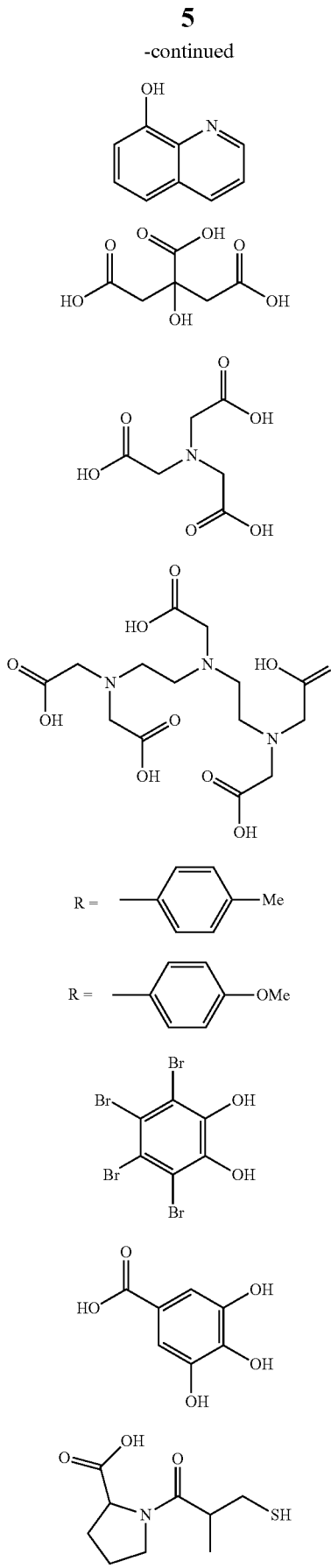
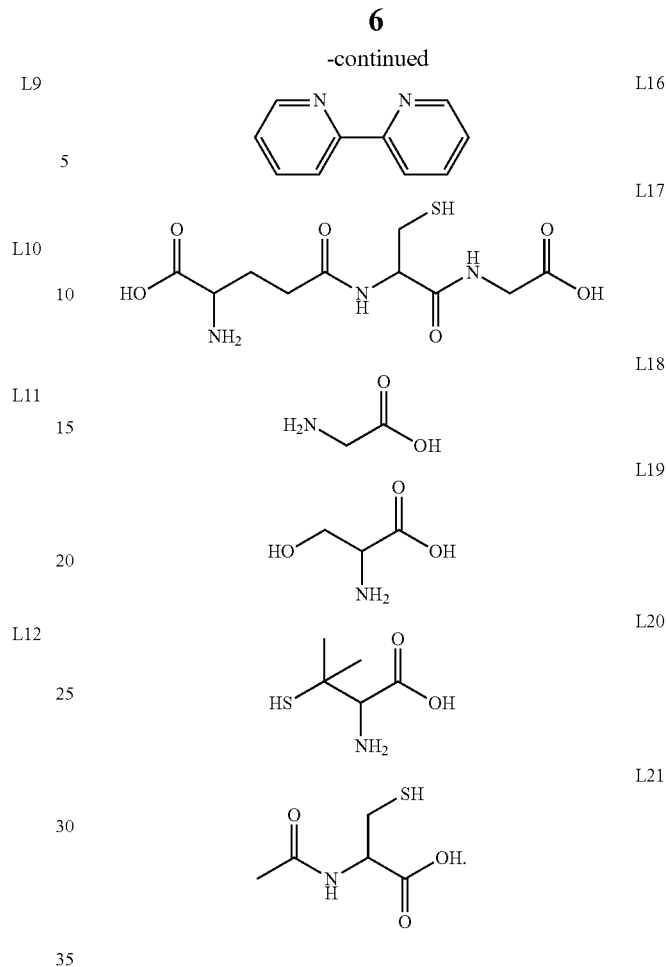

Provided herein are composition comprising a Bi(III) compound or pharmaceutically acceptable salt thereof. In certain embodiments, the Bi(III) compound or pharmaceutically acceptable salt thereof is a Bi(III) complex. In certain embodiments, the Bi(III) complex includes the complexes listed in Table 1.

Also provided are methods of using Bi(III) compounds for the modulation of MBL activity. Provided herein is a method of treating bacterial infection. Provided herein is a pharmaceutical composition comprising: (a) a β-lactam antibiotic; and (b) Bi(III) compounds or pharmaceutically acceptable salts thereof, as a medicament for the treatment of the MBL-producing bacterial infection. In certain embodiments, the Bi(III) compounds are bismuth subsalicylate ("BSS"), bismuth subgallate ("BSG"), colloidal bismuth subcitrate ("CBS") and ranitidine bismuth citrate ("RBC"). The composition described herein also exhibited potent anti-biofilm activity against bacterial biofilms that are resistant to currently available antibacterial agents. In certain embodiments, the composition is an antibacterial agent against a broad spectrum of bacterial infections. Also described herein is a composition comprising Bi(III) compounds. In certain embodiments, the composition is a pharmaceutical composition that includes solutions, suspensions, gels, fluid gels, emulsions, emulsion gels, lotions, ointments, film forming solutions, creams, sprays and lacquers. In particular, the antibacterial composition is used to treat or prevent local or systemic bacterial infection in a subject. In specific embodiment, the subject is a mammal. In specific embodiment, the subject is human. In one embodiment, provided herein is a method of treating bacterial infection comprising administering to a subject, a pharmaceutical formulation comprising a therapeutically effective amount of one or more antibacterial agents in combination with a Bi(III) compound.

4. BRIEF DESCRIPTION OF THE DRAWINGS

Figure 8:
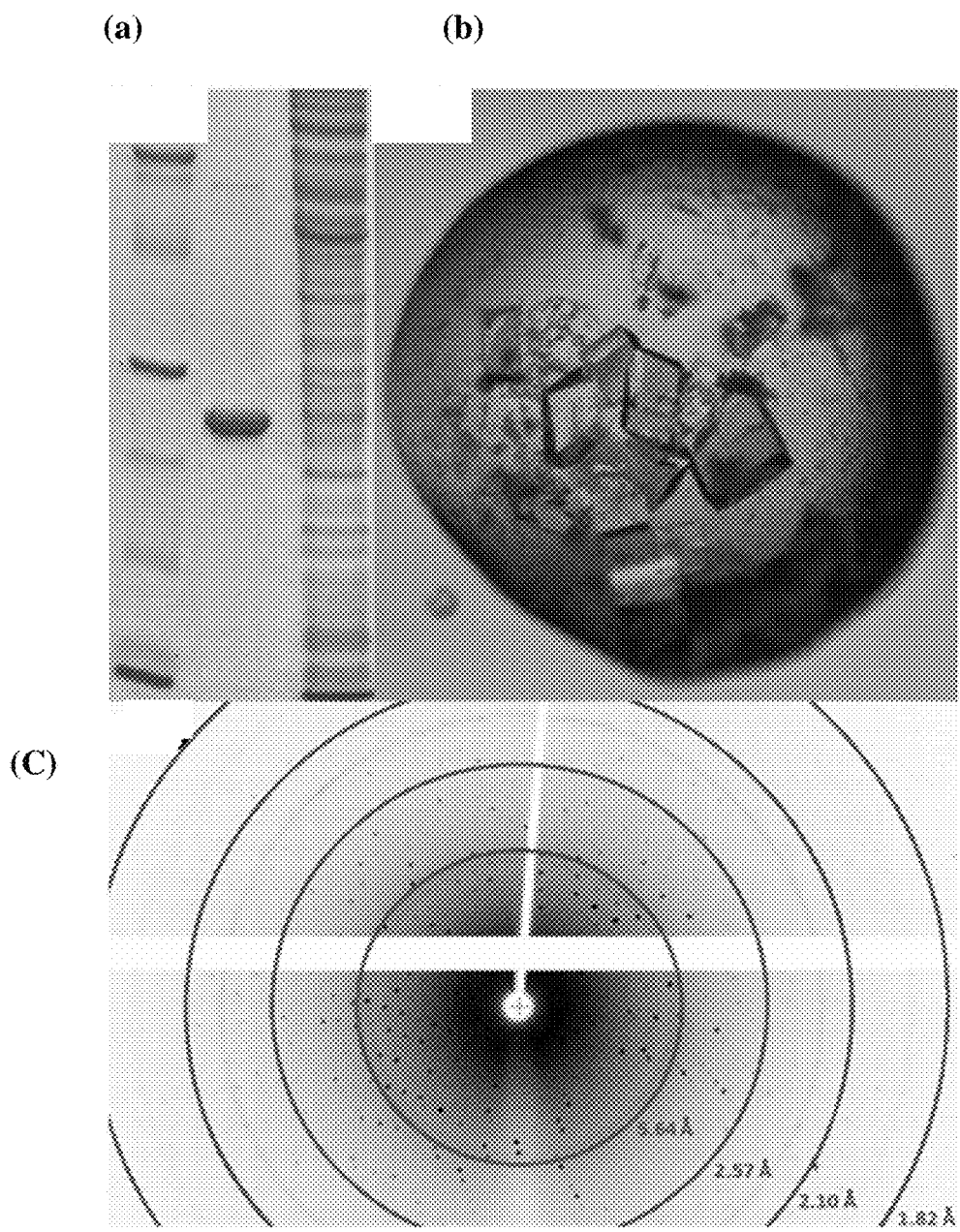

FIGS. 8 (a)-(c) show (a). SDS-PAGE of purified NDM-1 expressed in E. coli (BL21) cells harboring the NDM-1 gene in pET-28a vector. (b) A photo of the crystals grown from purified native NDM-1. (c) Diffraction image shows reasonable diffraction of the crystal (data were collected at BL17U1 station in Shanghai Synchrotron Radiation Facility).

Figure 9:
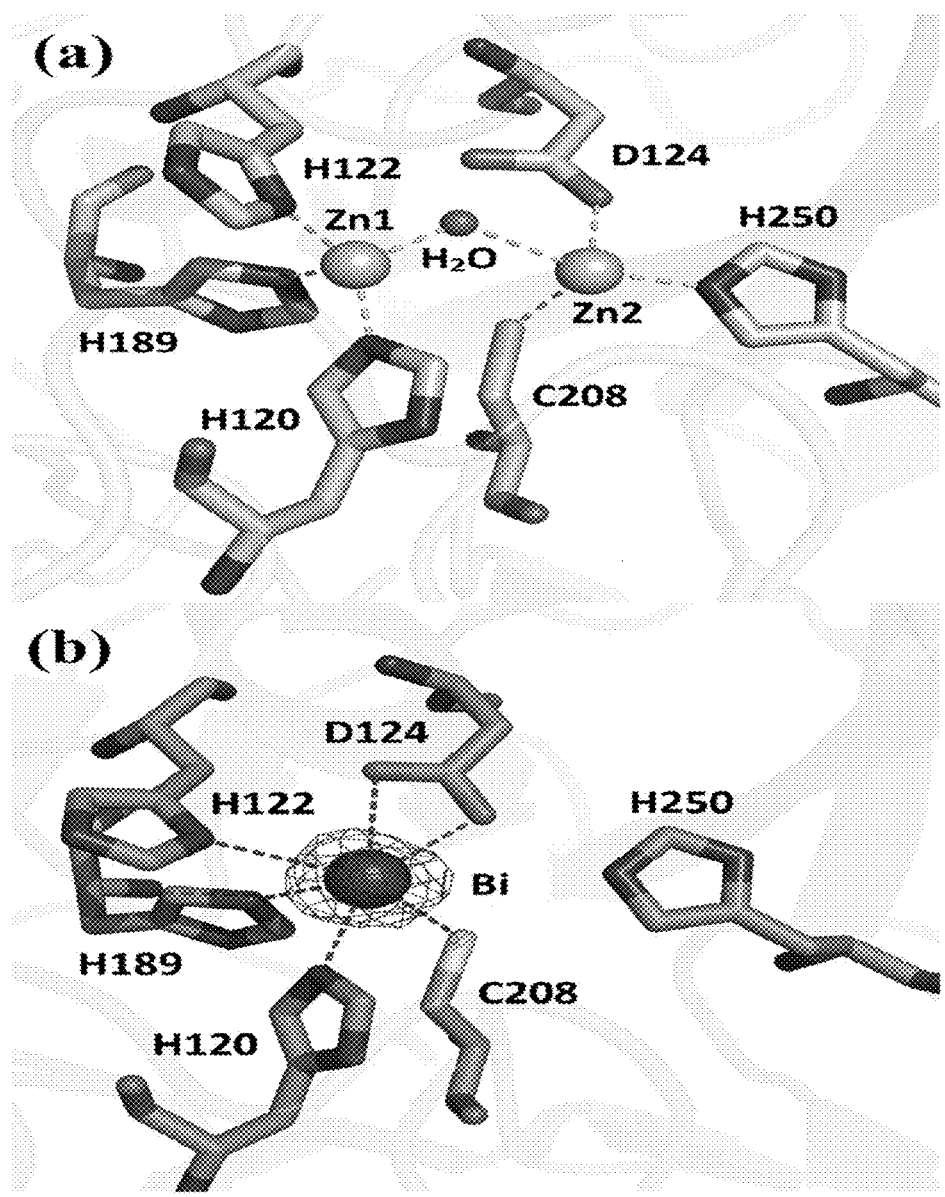

FIGS. 9 (a)-(b) show (a) X-ray structure of the active site of native NDM-1 with two Zn(II) ions shown in grey spheres and the bridging hydroxyl nucleophile in a red sphere. (b) X-ray structure of the active site of Bi-bound NDM-1 with the anomalous density of Bi contoured at 1σ shown in purple.

Figure 10:
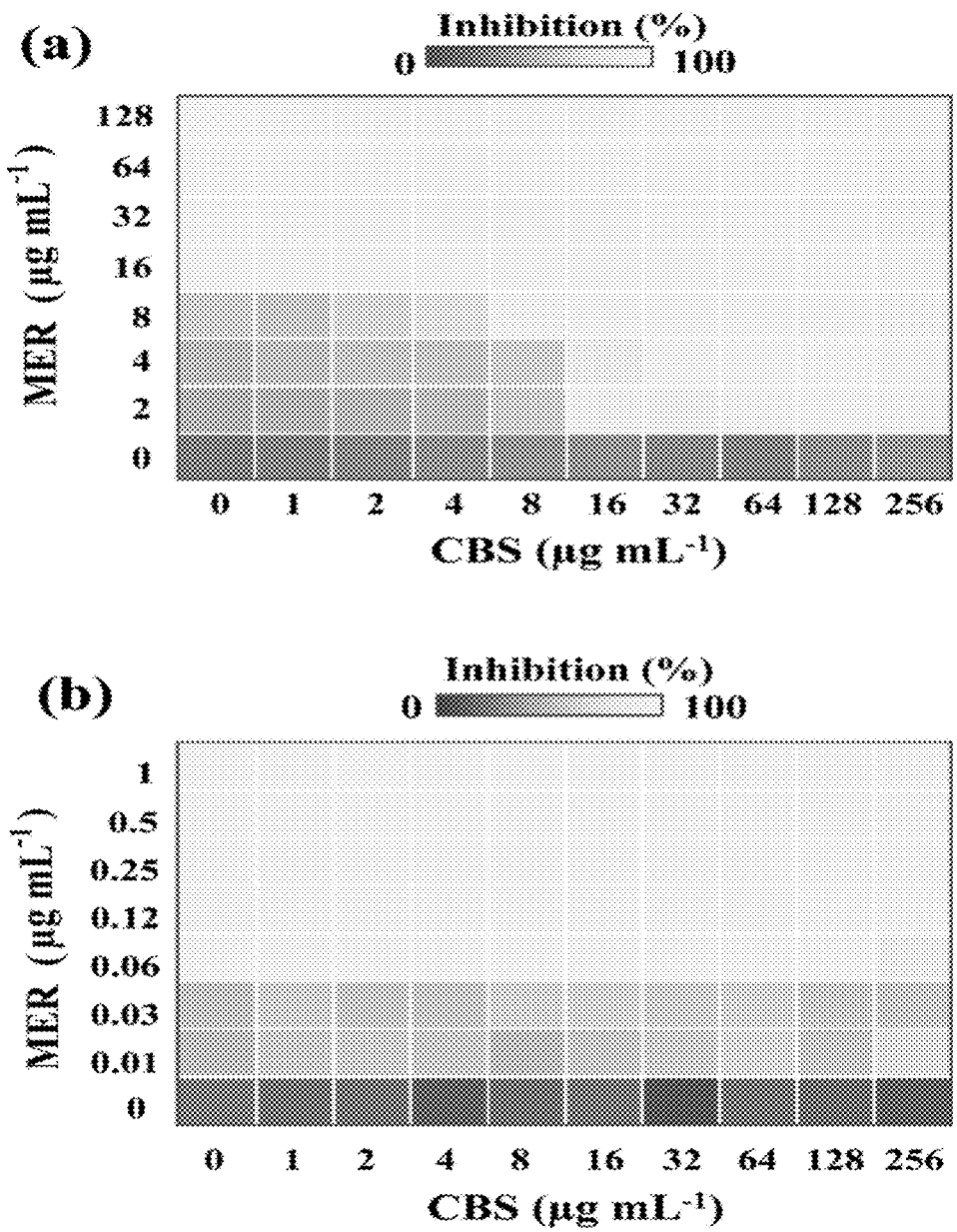

FIGS. 10 (a)-(b) show a heat map of checkerboard MIC analysis over MER and CBS against clinical isolates of (a) E. coli (NDM-1⁺) and (b) E. coli (NDM-1⁻).

Figure 11:
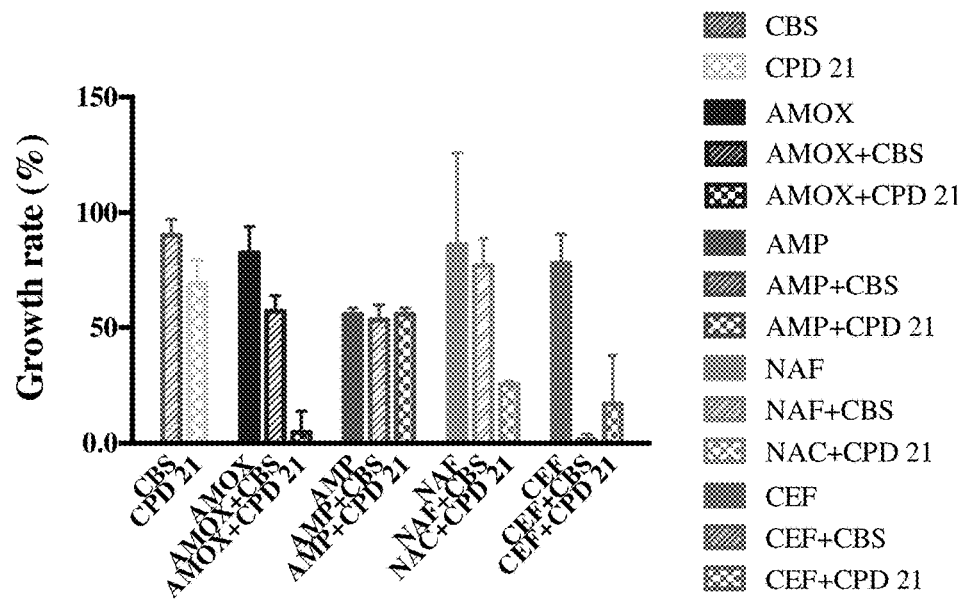

FIG. 11 shows the percent cell viability of E. coli (NDM-1⁺) upon the exposure to different antibiotics in the absence or presence of Bi(III) compounds. Note that evident restoration of activities of antibiotics was observed. The concentrations used in this test represent are: CBS 32 μg mL⁻¹, Bi-NAC 16 μg mL⁻¹, all the antibiotics 32 μg mL⁻¹. Abbreviation: AMOX: amoxicillin; AMP: ampicillin; NAF: nafcillin; CEF: cefdinir.

Figure 12:
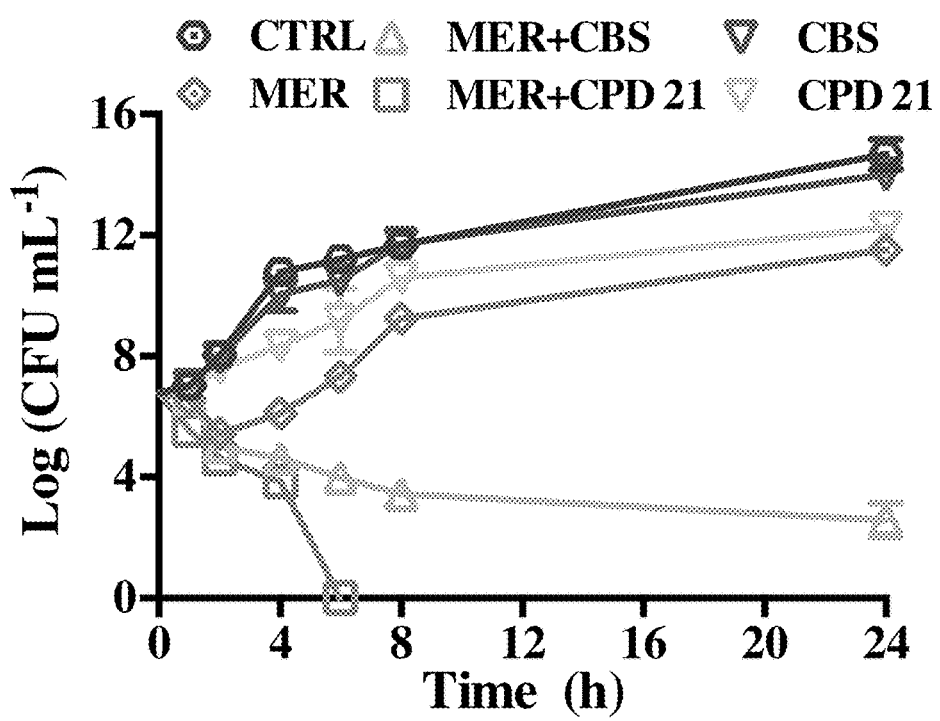

FIG. 12 shows a time-kill curves for log-phase growing E. coli (NDM-1⁺) upon treatment with MER, CBS and their combination for up to 24 hours. The concentrations of the drugs are 16 μg mL⁻¹ and 32 μg mL⁻¹ for MER and CBS, respectively.

Figure 13:
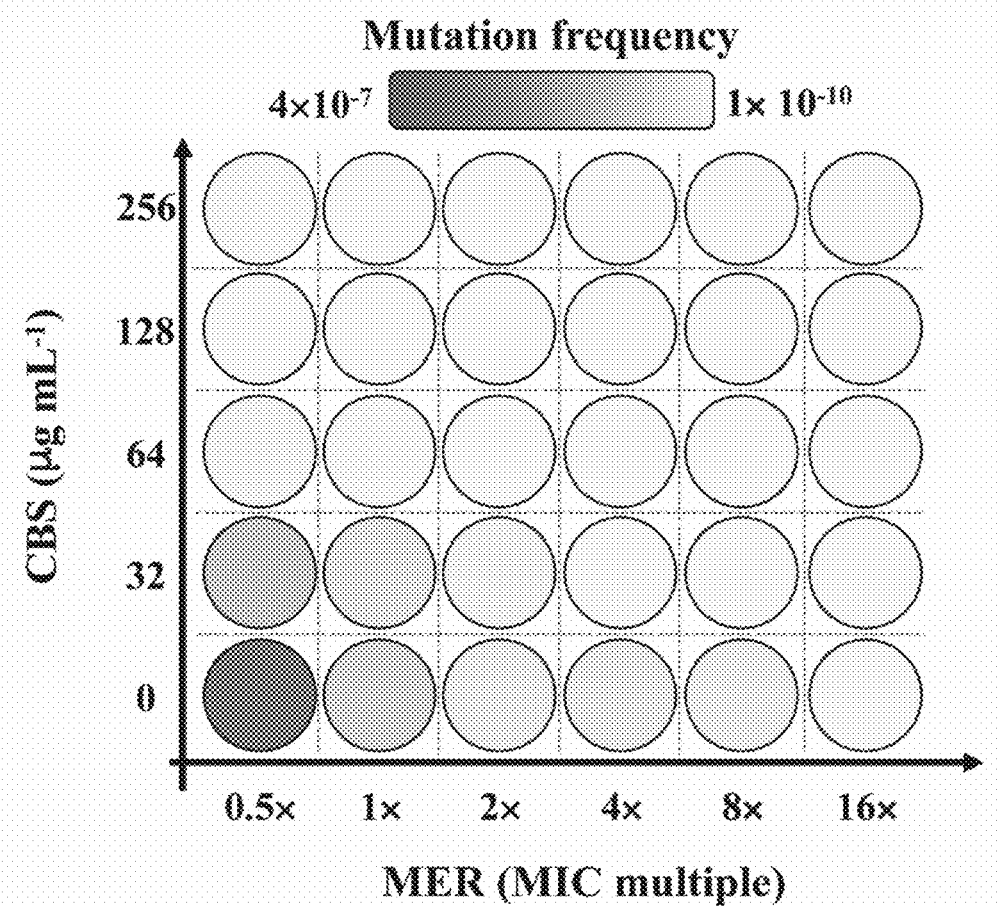

FIG. 13 shows a heat map of the mutation frequency of E. coli (NDM-1⁺) exposed to identical concentration of either MER or combination of MER and CBS.

Figure 14:
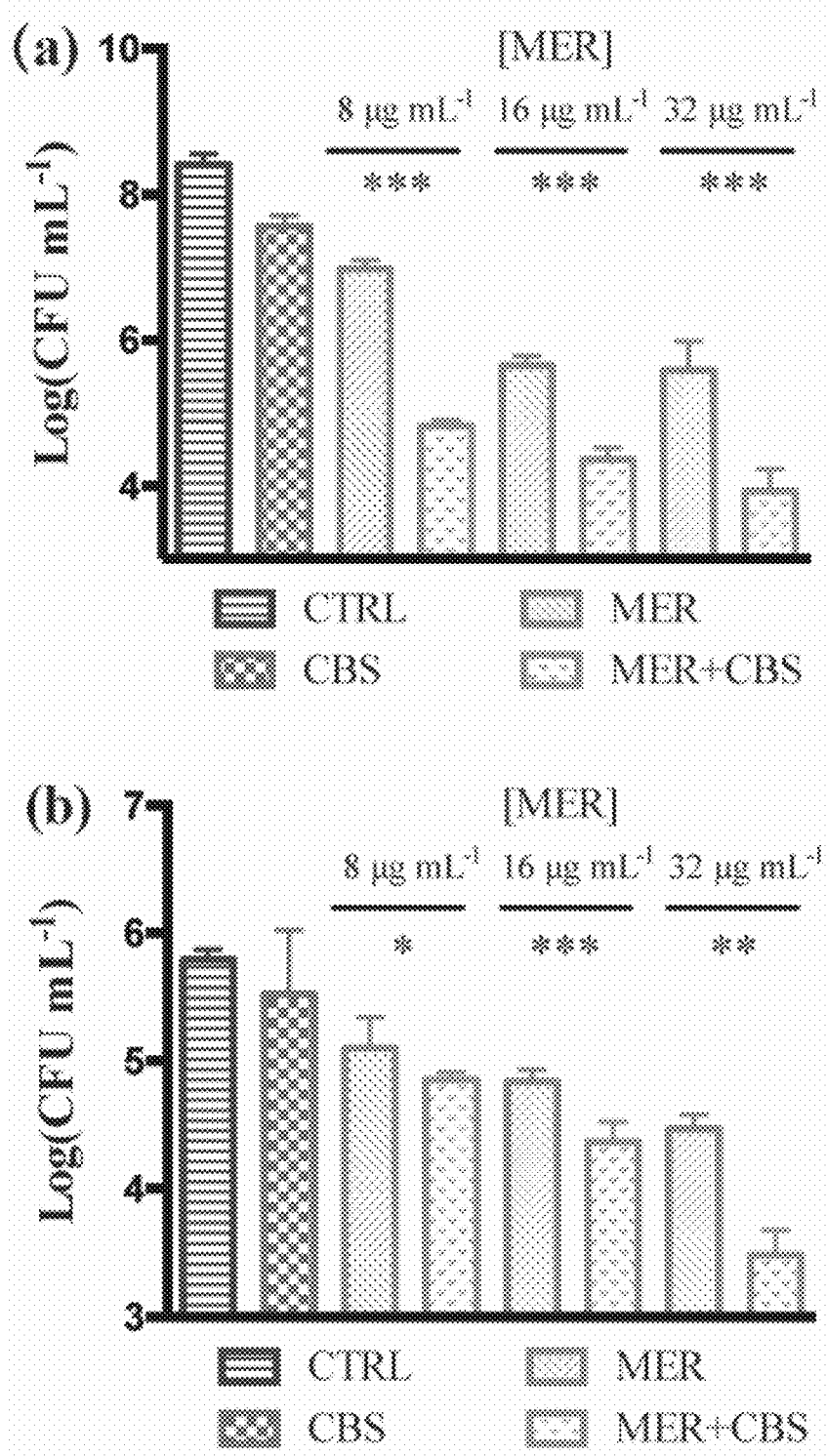

FIGS. 14 (a)-(b) show a bacterial density upon treatment of MER at escalating concentrations, in the absence or presence of CBS (32 μg mL⁻¹) in (a) cell-associated model and (b) cell-invaded model.

Figure 15:
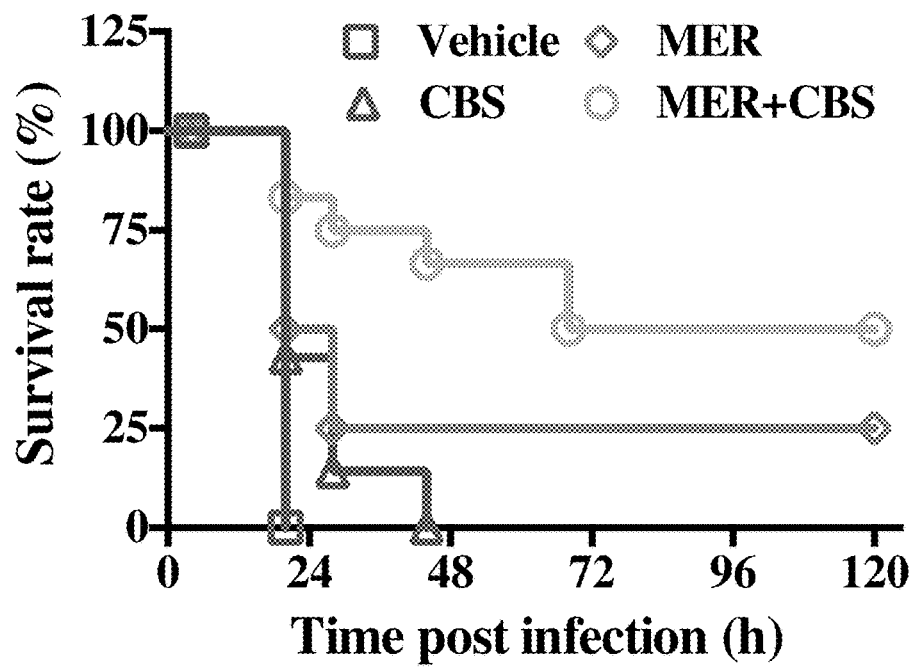

FIG. 15 is a survival curve showing efficacies in a murine peritonitis infection model. BALB/c mice were infected by a lethal dose of E. coli clinical isolate (NDM-1⁺) via i.p. injection and treated with one dose and 4 h post infection, followed by twice-daily treatment via i.p. injection. Five groups of mice were treated with MER (5 mg kg⁻¹), CBS (20 mg kg⁻¹), the combination of MER (5 mg kg⁻¹) and CBS (20 mg kg⁻¹), CBS (20 mg kg⁻¹, in the absence of bacteria) and PBS, respectively. P<0.001, Mantel-Cox test.

4.1 Definition

The term "antibiotics" herein refers to compounds that either kill or inhibit the growth of bacteria.

The term "metallo-β-lactamase" herein refers to a type of metallo-enzyme produced by bacteria endowing them resistance to β-lactam antibiotics by catalyzing the hydrolysis of the amide bond in the β-lactam rings, and thus demilitarizing their antibacterial properties.

The term "inhibitor" described herein refers to a molecule that binds to an enzyme and hinder the enzyme from its catalytic reaction.

The term "Bi(III) compounds" refers to bismuth drugs for example, including but not limited to bismuth subsalicylate ("BSS"), bismuth subgallate ("BSG"), citrate based bismuth compounds e.g. colloidal bismuth subcitrate ("CBS") and ranitidine bismuth citrate ("RBC"), or Bi(III) compounds comprise complexes with Bi(III) coordinated to but not limited to N, O or S containing ligands. The ligands involved include, but are not limited to,

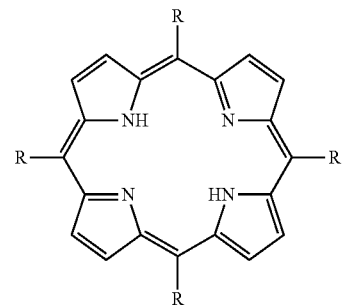

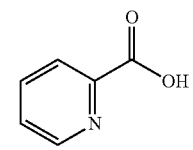

L5

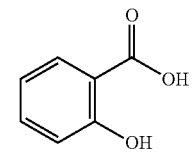

L6

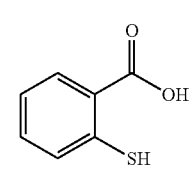

L7

-continued

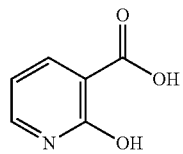

R = 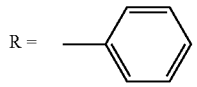

R = 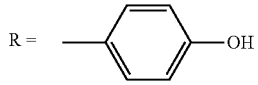

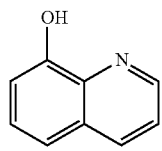

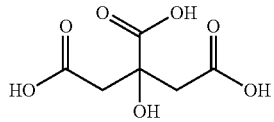

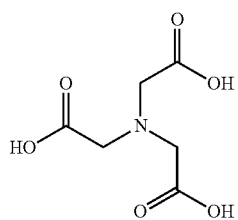

L3

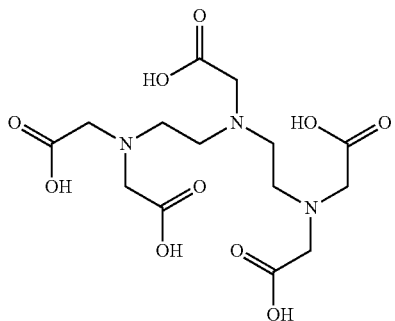

R = 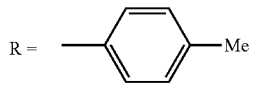

R = 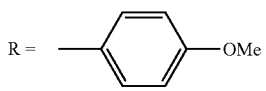

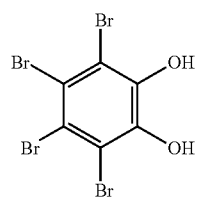

-continued

L8 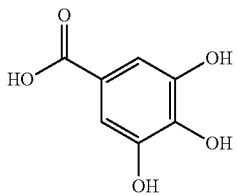

L1

L2

L9 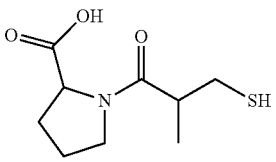

L10 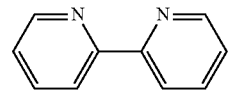

L11

L12

L4

L13

L14

L15

L16

L17

L18

L19

L20

L21

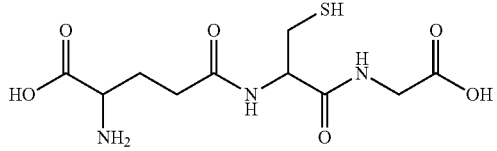

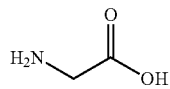

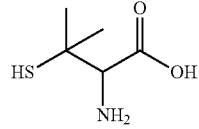

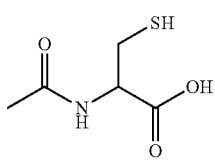

The term "cytotoxicity" refers to the property of being toxic to cells.

The term "MBL-producing bacterial pathogens" and "MBL-producing bacteria" refer to the bacterial pathogens that produce MBL(s) naturally or by the inducement of molecular biology reagent, such as isopropyl β-D-1-thiogalactopyranoside (IPTG).

The term "clinically relevant susceptible range" refers to the zone of inhibition or MICs at which an organism is considered to be susceptible based on obtainable serum concentrations of the drug, test compounds and clinical trials.

The term "synergistic effect" refers to the interaction between two or more compounds or chemicals when the combined effect is larger than the sum of the effects of the individual components.

The term "in vitro" refers to the experimentation carrying out with microorganisms, cells, and biological molecules outside their normal biological context. The term "in vivo" refers to experimentation using a whole, living organism as opposed to a partial or dead organism, which is most commonly represented by animal studies and clinical trials.

The term "biochemical methods" refers to those routine experimental techniques used in the field of biochemistry, which herein include molecular cloning, protein expression and purification as well as protein characterization. 'Molecular cloning' refers to a general method to engineer a desired DNA fragment into a vector for holding and preserving the fragment as well as directing their self-replications inside host cells for the ease of protein expression and purification. 'Protein expression' involves the use of some small molecules to stimulate host cells to produce the desired protein from the DNA intracellularly in a large amount enough for experimental uses. 'Protein purification', refers to separate the desired proteins from other unwanted molecules present inside cells so as to greatly enhance the homogeneity of the protein sample obtained.

The term "protein characterization" refers to the various physical and biochemical techniques used to elucidate the structure and function of a purified protein. The term 'metal content' refers to the ratio of metal ion(s) to a protein in various metallo-proteins. The term 'enzyme activity' refers to the molar quantity of substrate converted per unit time and is a standard parameter to evaluate and compare the reaction rate of an enzyme either in the presence or in the absence of inhibitors.

The term "pharmaceutically acceptable salt" refers to any salt(s) of a compound provided herein which retains its biological properties and which is not toxic or otherwise undesirable for pharmaceutical use. Such salts may be derived from a variety of organic and inorganic counter-ions well known in the art.

The term "solvate" includes a compound provided herein or a salt thereof, that further includes a stoichiometric or non-stoichiometric amount of solvent bound by non-covalent intermolecular forces.

The terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. The term "a subject in need thereof" refers to a subject having a bacterial infection, or a subject at risk of developing a bacterial infection. The subject may have been diagnosed as having such a bacterial infection as described herein or using standard medical techniques known to those of skill in the art. Alternatively a subject may exhibit one or more symptoms of bacterial infection.

The terms "compound", "agent" and "drug" are interchangeable.

The terms "therapeutic agent" and "therapeutic agents" refer to any agent(s) which can be used in the treatment or prevention of an infection. In certain embodiments, the term "therapeutic agent" includes a compound provided herein. In one embodiment, a therapeutic agent is an agent which is known to be useful for, or has been or is currently being used for the treatment or prevention of the infection.

The term "therapeutically effective amount" includes an amount of a compound or composition that, when administered to a subject for treating an infection, is sufficient to effect such treatment. A "therapeutically effective amount" can vary depending on, inter alia, the compound, the infection and its severity, and the age, weight, etc., of the subject to be treated.

The term "treating" or "treatment" of any infection refers, in one embodiment, to ameliorating the infection that exists in a subject. In another embodiment, "treating" or "treatment" includes ameliorating at least one physical parameter, which may be indiscernible by the subject. It is intended to include preventing, ameliorating, curing, reducing bacterial growth, or preventing any increase in bacterial growth.

The term "reducing bacterial growth" includes an interference in bacterial cell growth or processing which can be determined by a reduction in cell number, a reduction in cell division.

The term "about" refers to ±0.5 for a numerical value.

The term "resistant", "resistance" and "develop resistance" when refer to bacteria or bacterial infections that are no longer responsive to a compound or drug that was previously effective in reducing the bacterial growth or preventing any increase in bacterial growth.

5. DETAILED DESCRIPTION

5.1 Metallo-β-Lactamases Inhibitors

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter. It is to be understood that particular features, structures, or characteristics described may be combined in various ways in one or more implementations.

Provided herein is a novel type of wide-spectrum MBLs inhibitor—Bi(III) compounds or the pharmaceutically acceptable salts thereof, that modulate MBLs activity via a metal replacement mechanism. Provided herein are methods to treat infection from MBL-producing bacteria by administering the MBLs inhibitors with β-lactam antibiotics.

Provided herein are methods of preparing Bi(III) compounds by repositioning of Bi(III) compounds and coordinating Bi(III) to N, O, or S containing ligands. Examples of the ligands of Bi (III) include, but are not limited to,

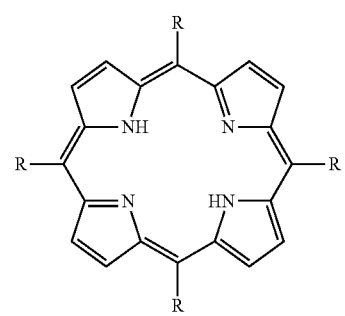

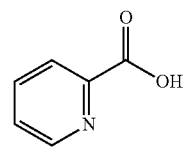

L5

-continued
L6
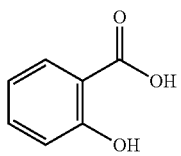
L7
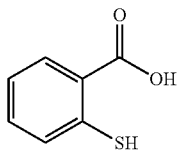
L8
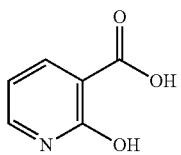
L1
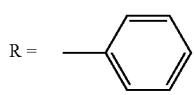
L2
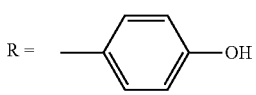
L9
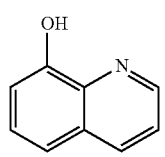
L10
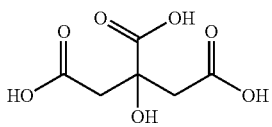
L11
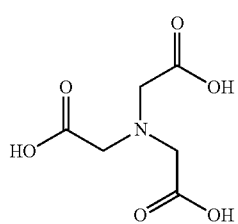
L12
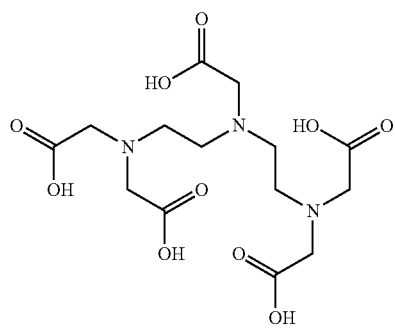
L3
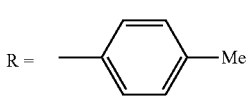
-continued
L4
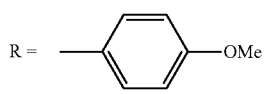
L13
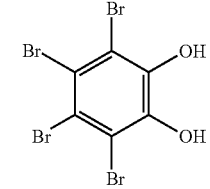
L14
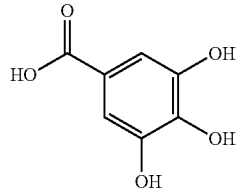
L15
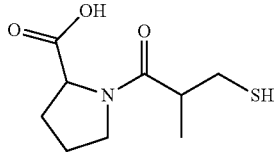
L16
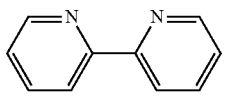
L17
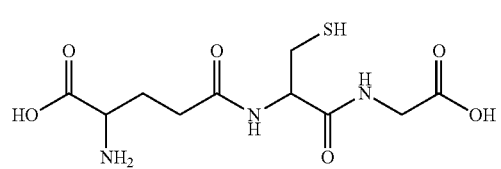
L18
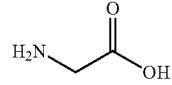
L19
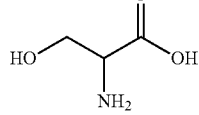
L20
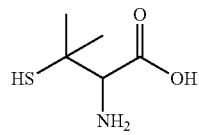
L21
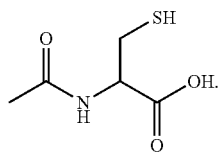
Provided herein are composition comprising a Bi(III) compound or pharmaceutically acceptable salt thereof. In certain embodiments, the Bi(III) compound or pharmaceutically acceptable salt thereof is a Bi(III) complex. In certain embodiments, the Bi(III) complex includes the complexes listed in Table 1.

In certain embodiments, the β-lactam antibiotic and the MBLs inhibitor have a molar ratio ranging from 1:16, 2:15, 3:14, 4:13; 5:12, 6:11, 7:10, 8:9, 9:8, 10:7, 11:6, 12:5, 13:4, 14:3, 14:3, 15:2, 16:1 by weight (w/w). In certain embodiments, the β-lactam antibiotic and the MBLs inhibitor have a molar ratio ranging from 1:16 to 16:1 by weight (w/w).

β-lactam antibiotics are a broad class of antibiotics which are characterized by their four-membered, nitrogen-containing beta-lactam ring at the core of their structure. Examples of β-lactam antibiotics include, but not limited to penicillin derivatives (penams), cephalosporins (cephems), carbapenems, and monobactams.

In one embodiment, the β-lactam antibiotic is meropenem ("MER") which belongs to carbapenem and has extended-broad-spectrum antibacterial activity against a wide variety of bacteria. Similar to other β-lactam antibiotics, the beta-lactam ring portion of MER binds to different DD-transpeptidases, viz, penicillin-binding proteins ("PBPs") in cell membrane rendering them unable to perform their roles in synthesis of the peptidoglycan layer of bacterial cell wall. This results in the bacterial death owing to osmotic instability or autolysis. The structure of MER is represented by the following formula:

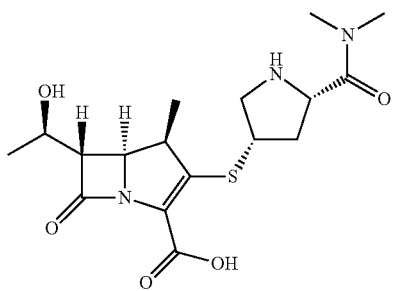 [SMILES: C[C@@H](O)[C@H]1C(=O)N2C(C(=O)O)=C(S[C@@H]3CN[C@H](C(=O)N(C)C)C3)[C@H](C)[C@H]12]

The mechanism of action of Bi(III) is unveiled via X-ray crystallography which showed that one bismuth ion replaced two zinc ions, leading to inactivation of the MBLs. Based on the fact that MBLs are inactivated in these bacteria through the same mechanism, Bi(III) compounds or the pharmaceutically acceptable salts thereof disclosed herein serve as wide-spectrum inhibitors of MBLs. In some embodiments, Bi(III) compounds or the pharmaceutically acceptable salt thereof, exhibited no or negligible in vitro cytotoxicity to human cells. In some embodiments, the bismuth compounds showed good inhibitory activity on MBLs. Upon the use of Bi(III) compounds or the pharmaceutically acceptable salt thereof, β-lactam antibiotic shows revived antimicrobial activity and prevents the growth or kills MBL-producing bacteria at clinically relevant susceptible range. In one embodiment, the combination of MER and CBS exerts synergistic effect in the treatment of in vitro bacterial infection. In certain embodiments, MER show boosted efficacy in an in vivo murine peritonitis infection model when co-administered with CBS. In certain embodiments, the antibacterial efficacy of the Bi(III) complexes or the pharmaceutically acceptable salt thereof is enhanced by 2-4, 4-6, 6-8 folds as compared to antibiotics that are without the Bi (III) complexes or the pharmaceutically acceptable salt thereof. In certain embodiments, the antibacterial efficacy of MER is enhanced by 4-8 folds in the presence of Bi(III) compound or the pharmaceutically acceptable salt thereof as compared to MER alone.

In some embodiments, Bi(III) center of different complexes exist in the form of monomer, dimer or polymer in solution. The Bi(III) coordination core usually is negatively charged, thus requires at least one counter-cation to achieve electric neutrality. In certain embodiments, pharmaceutically acceptable salts thereof include those generated from charged bismuth complexes and counter cation and/or anion.

In certain embodiments, MBLs require Zn(II) for the catalysis and are able to hydrolyze β-lactam antibiotics. Examples include, but not limited to, BCII, CcrA, IMP, VIM, NDM and DIM. In some embodiments, the β-lactamase includes NDM-1, VIM-2, and IMP-4.

In some embodiments, the inhibitors refer to Bi(III) compounds or the pharmaceutically acceptable salts thereof.

Bi (III) compounds or the pharmaceutically acceptable salts thereof described herein relate to stable Bi(III) compounds or the pharmaceutically acceptable salts thereof. Bi(III) compounds comprise complexes with Bi(III) coordinated to but not limited to N, O or S containing ligands. The ligands involved include, but are not limited to,

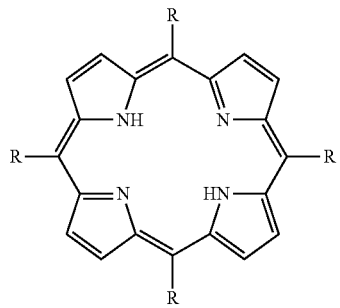

L5

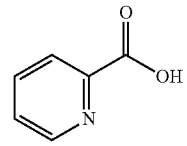

L6

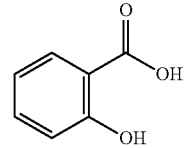

L7

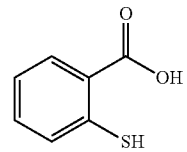

L8

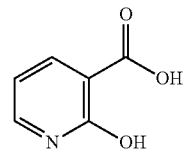

L1

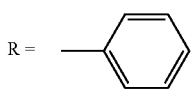

R = 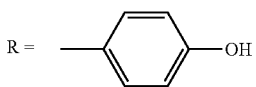

L9
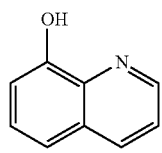

L10
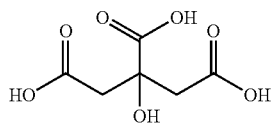

L11
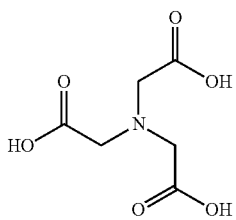

L12
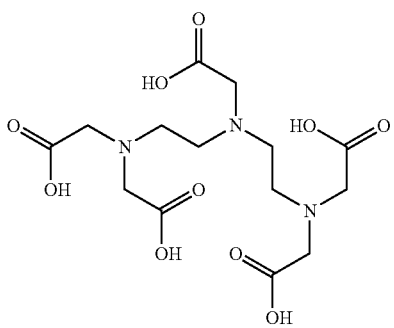

L3

R = 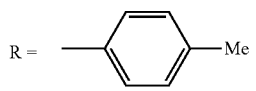

L4

R = 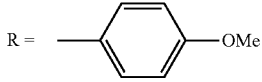

L13
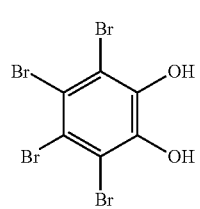

L14
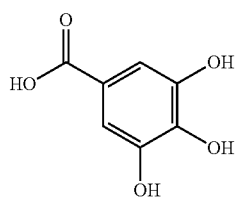

L2
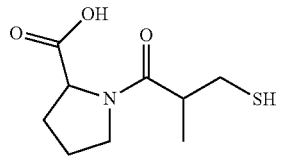

L15
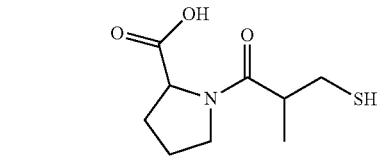

L16
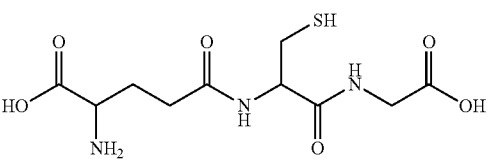

L17
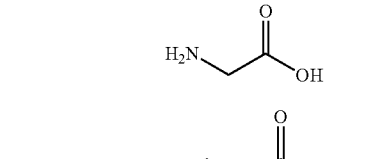

L18
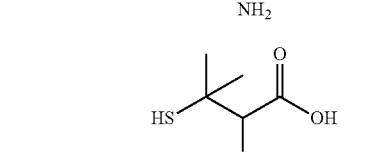

L19
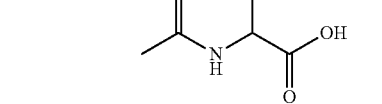

L20

L21

Given that cells exposed to a cytotoxic substance may undergo necrosis, where they lose membrane integrity and die rapidly due to cell lysis; or they may discontinue growing and proliferating; or they may initiate apoptosis, which is a genetic program of controlled cell death. In one embodiment, XTT assay is used to examine the cytotoxicity of Bi(III) complexes to human cells. The human cell lines include, but not limited to human hepatocyte cell line (MIHA).

In some embodiments, examples of MBL producing bacteria include, but not limited to some enterobacterial strains, such as *E. coli* (NDM-1$^+$), *E. coli* (VIM-2$^+$), *E. coli* (IMP-4$^+$), *K. pneumonia* (NDM-1$^+$) and *C. freundii* (NDM-1$^+$).

In one specific embodiment, the clinically relevant susceptible range of carbapenem towards Enterobacteriaceae is ≤2 mg mL-1 according to the criteria of European Committee on Antimicrobial Susceptibility Testing (EUCAST).

In some specific embodiments, the synergistic effect is quantified by the calculation of fractional inhibitory concentration index (FICI).

In one specific embodiment, madin-darby canine kidney (MDCK) cells are chosen as the context for in vitro bacterial infection experiment. In one specific embodiment, BALB/c mice are chosen as the context for in vivo murine infection experiment.

In some embodiments, the mechanism of the inhibition of purified NDM-1 was investigated by determining the 'metal content' and the 'enzyme activity' of NDM-1 protein. About a quarter to 30% of proteins in humans and microbes are found to bind to various important metal ions to exert their in vivo functions and they are generally regarded as 'metallo-proteins'. In some embodiments, both the Bi(III) and Zn(II) contents were studied.

In one embodiment, the purified NDM-1 was crystallized and incubated with Bi(III) compounds followed by X-ray diffraction experiments to generate a three dimensional structural data of the protein. The binding of Bi(III) to the protein was then observed using suitable structural biology computer software as described in the example section below.

5.2 Combination Therapy

The compounds as described herein may be optionally delivered with other antibacterial agents in the form of antibacterial cocktails, or individually, yet close enough in time to have a synergistic effect on the treatment of the infection. An antibacterial cocktail is a mixture of any one of the compounds described herein with another antibacterial drug. In one embodiment, a common administration vehicle (e.g., tablet, implants, injectable solution, injectable liposome solution, etc.) is used in for the compound as described herein and other antibacterial agent(s).

5.3 Pharmaceutical Compositions

The compound disclosed herein can be formulated into pharmaceutical compositions using methods available in the art and those disclosed herein. Such compounds can be used in some embodiments to enhance delivery of the compound to the subject.

The methods provided herein encompass administering pharmaceutical compositions containing at least one compound as described herein, if appropriate in the salt form, either used alone or in the form of a combination with one or more compatible and pharmaceutically acceptable carriers, such as diluents or adjuvants, or with another antibacterial agent. In certain embodiments, the second agent can be formulated or packaged with the compound provided herein, according to those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art. In clinical practice the active agents provided herein may be administered by any conventional route, in particular orally, parenterally, rectally or by inhalation (e.g. in the form of aerosols). In certain embodiments, the compound provided herein is administered orally. Use may be made, as solid compositions for oral administration, of tablets, pills, hard gelatin capsules, powders or granules. In these compositions, the active product is mixed with one or more inert diluents or adjuvants, such as sucrose, lactose or starch. These compositions can comprise substances other than diluents, for example a lubricant, such as magnesium stearate, or a coating intended for controlled release. Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products. The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium. The compositions for rectal administration are suppositories or rectal capsules which contain, in addition to the active principle, excipients such as cocoa butter, semisynthetic glycerides or polyethylene glycols. The compositions can also be aerosols. For use in the form of liquid aerosols, the compositions can be stable sterile solutions or solid compositions dissolved at the time of use in sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose. In one embodiment, a composition provided herein is a pharmaceutical composition or a single unit dosage form. Pharmaceutical compositions and single unit dosage forms provided herein comprise a therapeutically effective amount of one or more therapeutic agents (e.g., a compound provided herein, or other prophylactic or therapeutic agent), and one or more pharmaceutically acceptable carriers or excipients. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin. Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents. Lactose free compositions provided herein can comprise excipients that are well known in the art and are listed, for example, in the U.S. Pharmocopia. In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate. Further encompassed herein are anhydrous pharmaceutical compositions and dosage forms comprising active ingredients, since water can facilitate the degradation of some compounds. Anhydrous pharmaceutical compositions and dosage forms provided herein can be prepared using anhydrous or low moisture containing ingredients and low moisture or low humidity conditions. An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs. The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject. The composition, shape, and type of dosage forms provided herein will typically vary depending on their use. For example, a dosage form used in the initial treatment of bacterial infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000). Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound. Oral Dosage Forms Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, provided herein is a hand sanitizing composition comprising the compounds disclosed herein. In certain embodiments, provided herein is a lotion comprising the compounds as disclosed herein.

5.4 Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing a bacterial infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the infection, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In one embodiment, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different infections, as will be readily known by those of ordinary skill in the art. Similarly, amounts sufficient to prevent, manage, treat or ameliorate such infections, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate an infection, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate an infection, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses. In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL. In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months. In certain aspects, provided herein are unit dosages comprising a compound, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art. The dosages of the second agents are to be used in the combination therapies provided herein. In certain embodiments, dosages lower than those which have been or are currently being used to prevent or treat bacterial infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics 9.sup.th Ed, Mc-Graw-Hill, New York; Physician's Desk Reference (PDR) 57.sup.th Ed., 2003, Medical Economics Co., Inc., Montvale, N.J., which are incorporated herein by reference in its entirety.

In various embodiments, the therapies (e.g., a compound provided herein and a second agent in a combination therapy) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In various embodiments, the therapies are administered no more than 24 hours apart or no more than 48 hours apart. In certain embodiments, two or more therapies are administered within the same patient visit. In other embodiments, the compound provided herein and the second agent are administered concurrently. In other embodiments, the compound provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the compound provided herein and the second active agent exert their effect at times which overlap. Each second active agent can be administered separately, in any appropriate form and by any suitable route. In other embodiments, the compound provided herein is administered before, concurrently or after administration of the second active agent. In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment. In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day. The second agent can act additively or synergistically with the compound provided herein. In one embodiment, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

5.5 Patient Population

In some embodiments, a subject treated for infection in accordance with the methods provided herein is a human who has or is diagnosed with an infection. In other embodiments, a subject treated for infection in accordance with the methods provided herein is a human predisposed or susceptible to infection. In some embodiments, a subject treated for infection in accordance with the methods provided herein is a human at risk of developing infection.

In one embodiment, a subject treated for infection in accordance with the methods provided herein is a human infant. In another embodiment, a subject treated for infection in accordance with the methods provided herein is a human toddler. In another embodiment, a subject treated for infection in accordance with the methods provided herein is a human child. In another embodiment, a subject treated for infection in accordance with the methods provided herein is a human adult. In another embodiment, a subject treated for infection in accordance with the methods provided herein is a middle-aged human. In another embodiment, a subject treated for infection in accordance with the methods provided herein is an elderly human.

In some embodiments, a subject treated for infection in accordance with the methods provided herein that has a recurrence of the infection.

In certain embodiments, a subject treated for infection in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for infection in accordance with the methods provided herein is a human that is 18 years old or older. In a particular embodiment, a subject treated for infection in accordance with the methods provided herein is a human child that is between the age of 1 year old to 18 years old. In a certain embodiment, a subject treated for infection in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for infection in accordance with the methods provided herein is administered a pharmaceutical composition thereof, or a combination therapy before any adverse effects or intolerance to therapies.

In some embodiments, a subject treated for infection accordance with the methods provided herein is a human that has established resistance to previous antibiotic therapies other than treatment with the presently disclosed therapy. In certain embodiments, a subject treated for infection in accordance with the methods provided herein is a human already receiving one or more conventional antibacterial therapies. Among these patients are patients who have developed infections that are resistant to antibiotics and patients with recurring infections despite treatment with existing therapies. In certain embodiments, the patients have been previously treated with β-lactum antibiotics. In certain embodiments, the patients have been previously treated with carbapenem. In certain embodiments, the patients have been previously treated with meropenem, imipenem, ertapenem, doripenem, biapenem, faropenem, panipenem, razupenem, tebipenem, tomopenem or a combination thereof. In certain embodiments, the patients have developed infections that are resistant to β-lactum antibiotics. In certain embodiments, the patients have developed infections that are resistant to carbapenem. In certain embodiments, the patients have developed infections that are resistant to meropenem, imipenem, ertapenem, doripenem, biapenem, faropenem, panipenem, razupenem, tebipenem, tomopenem or a combination thereof.

5.6 Kits

Also provided are kits for use in methods of treatment of a bacterial infection. The kits can include a compound or composition provided herein, a second agent or composition, and instructions providing information to a health care provider regarding usage for treating the infection. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition. In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

The kits described herein contain one or more containers, which contain compounds, signaling entities, biomolecules and/or particles as described. The kits also contain instructions for mixing, diluting, and/or administrating the compounds. The kits also include other containers with one or more solvents, surfactants, preservative and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits comprise a carrier being compartmentalized to receive in close confinement one or more container such as vials, tubes, and the like, each of the container comprising one of the separate elements to be used in the method. For example, one of the container may comprise a positive control in an assay. Additionally, the kit may include containers for other components, for example, buffers useful in the assay.

5.7 Method of Treatment

Provided herein is a method of reducing growth of a bacteria by administering one or more compounds provided herein. The method comprises contacting a cell with one or more compounds as described herein in an amount effective to reduce the growth of bacteria. Provided herein are methods for treating a bacterial infection in a subject by administering to a subject in need thereof the compounds described herein in an amount effective to reduce the growth of bacteria.

5.8 Methods of Coating a Medical Device

The compounds that are provided herein can be used to treat a variety of medical devices, such as catheters, as well as industrial surfaces. Bacteria can form biofilm on intravascular catheters and other medical implants. These biofilms enhance antimicrobial resistance and can render infections refractory to antibacterial therapy. Persistence of an infection can necessitate removal of the device, which can be undesirable or even life threatening. Therefore, provided herein is a method of coating a medical device using the compounds described herein on the materials or surfaces of the medical device that mitigate or prevent bacterial colonization or infection with subsequent biofilm formation. The method comprises applying the composition described herein on the surface of a medical device. In certain embodiments, the composition adheres to the surface of a medical device. In certain embodiments, the composition is coated in the medical device.

In certain embodiments, provided herein is a composition comprising a paint and one or more compounds as described herein. Also provided is a method of modifying a surface of a medical device. The method comprises providing one or more coatings of a composition, comprising one or more compounds as described herein, to at least a portion of the surface of a medical device to form a coated surface region. In certain embodiments, the medical device is an implantable medical device. In certain embodiments, the industrial surface is stainless steel. In certain embodiments, the industrial surface is plastic. In certain embodiments, the industrial surface is a surgical table. In certain embodiments, the medical device is a surgical instrument.

The following Examples illustrate the synthesis and use of representative compounds provided herein. These examples are not intended, nor are they to be construed, as limiting the scope of the claimed subject matter. It will be clear that the scope of subject matter may be practiced otherwise than as particularly described herein. Numerous modifications and variations of the subject matter are possible in view of the teachings herein and, therefore, are within the scope the claimed subject matter.

6. EXAMPLES

6.1. Example 1: Preparation of the Exemplary Bismuth Complexes

6.1.1 Synthesis of Complex 1, 2, 3 and 4

Complexes 1, 2, 3 and 4 were synthesized. Take the synthesis of complex 1 for instance, 5,10,15,20-tetraphenyl-21H-23H-porphine (L1, 0.20 mmol) was added to pyridine (50 mL) and the temperature was increased until the purple solution was refluxing. $Bi(NO_3)_3.5H_2O$ (2.10 mmol) was then added and the solution was left to reflux for 3 hours. More $Bi(NO_3)_3.5H_2O$ (4.10 mmol) was added and the solution was left to reflux for a further 5 hours. The resulting dark-green solution was then left to cool to room temperature before the bulk of the pyridine solvent was removed via rotary evaporation. The resulting green mixture was then left to dry overnight under vacuum to remove any remaining solvents. The green solid obtained was then washed with chloroform (20 mL) and rotary evaporated to ensure that all pyridine was removed. This was repeated for 5 times followed by overnight drying under vacuum. Dark green solid was then purified on a silica gel column. The compound was loaded onto the column using a dry method and the product was obtained by eluting the column with chloroform and methanol in a ratio of 20:1.

6.1.2 Synthesis of Complex 5

$Bi(NO_3)_3.5H_2O$ (1.00 mmol) was added to deionized water (50 mL) resulting in a cloudy white solution. The temperature was increased until the solution was refluxing and had turned colorless. At this point, 2-picolinic acid (3.00 mmol) (L5) was added and the resulting colorless solution was left to reflux for 2 hours. The solution was then allowed to cool to room temperature before being filtered under vacuum to remove any insoluble impurities. The colorless filtrate was then decanted into a beaker, covered and allowed to stand at room temperature for 2 days after that small amounts of small, colorless crystals of complex, suitable for x-ray analysis, were obtained. The crystalline product was then collected via vacuum filtration.

6.1.3 Synthesis of Complex 7

Bismuth complexation with thiosalicylic acid (L7) was prepared by dissolving $Bi(NO_3)_3.5H_2O$ (1.00 mmol) and thiosalicylic acid (2.50 mmol) in DMSO (15 mL), followed by sonication till dissolving. The mixture was stirred at room temperature for 0.5 hour and then extracted by water and ethyl acetate. The final product was obtained by recrystallizing and washed by water and saturated NaCl solution and then dried in vacuum.

6.1.4 Synthesis of Complex 8

$Bi(NO_3)_3.5H_2O$ (1.00 mmol) was refluxed in deionised water (15 mL) until solution turned colorless. 2-hydroxynicotinic acid (1.00 mmol) (L8) was added and the mixture was refluxed for an overnight. Any remaining solid was filtered off and the filtrate was left at 4° C. for several days. A small yield of off-white solid formed and was washed with small volume of deionized water. This left a white insoluble solid and a yellow aqueous solution. The solution was left for crystal formation.

6.1.5 Synthesis of Complex 9

$Bi(NO_3)_3.5H_2O$ (1.00 mmol) was dissolved in ethanol (60 mL), with stirring, at room temperature for 0.5 hour, followed by the addition of 8-hydroxyquinoline (3.00 mmol) (L9). The solution, which immediately turned yellow upon addition of the ligand, was left to reflux for 3 hours after that it was left to cool to room temperature. The cloudy yellow solution was then filtered under vacuum and the clear, yellow filtrate was collected. Triethylamine and deionized water were then added to cause immediate precipitation of a yellow solid. The solution was again vacuum filtered and the yellow powder was left to dry under vacuum overnight.

6.1.6 Synthesis of Complex 11 and 12

Complexes 11 and 12 were synthesized via a generic method. Take the synthesis of complex 12 for instance, firstly $(BiO)_2CO_3$ (2.50 mmol) was slowly added to hot EDTA-water solution (100 mL). The mixture was refluxed for 4 hours on oil bath and then filtered while hot. The filtrate was settled at 4° C. for one or two days and afforded small crystal by slow evaporation.

6.1.7 Synthesis of Complex 13

Bismuth complex with tetrabromocatechol (L13) was prepared by dissolving $Bi(NO_3)_3.5H_2O$ (1.00 mmol) and L13 (1.00 mmol) in DMSO (20 mL) and stirring at room temperature for 1 hour. The solution was then extracted by water and ethyl acetate, followed by evaporation. The final product was washed by water and saturated NaCl solution and then dried in vacuum.

6.1.8 Synthesis of Complex 15

$BiCl_3$ (1.00 mmol) dissolved in methanol (15 mL), followed by addition of HCl (37%, 50 µL). Captopril (3.00 mmol) (L15) was added and mixture was stirred overnight at room temperature at pH 2. Sodium hydroxide was added to increase pH to 10. The solution changed its colour to orange. Methanol was removed in vacuum, and the resulting solid was filtered and washed with minimum volume ethanol.

6.1.9 Synthesis of Complex 16

$Bi(NO_3)_3.5H_2O$ (1.00 mmol) and 2,2'-bipyridine (2.00 mmol) (L16) were dissolved, with gentle heating, in a minimum amount of DMSO. Once fully dissolved, the warm colorless solution was filtered and the colorless filtrate was left to stand at room temperature for 14 days to yield a small amount of pale pink crystals, suitable for x-ray analysis. The crystalline product was then collected via vacuum filtration.

6.1.10 Synthesis of Complex 17

$Bi(NO_3)_3 \cdot 5H_2O$ (1.00 mmol) and reduced form of glutathione (2.00 mmol) (L17) were dissolved in deionized water (20 mL), sonicated and left to stir at room temperature for 0.5 hour. The solution was then filtered to remove any insoluble impurities and then slowly rotary evaporated to remove most water. Then the wet sample was left in freeze drier overnight and collect solid product then.

6.1.11 Synthesis of Complex 20

$BiCl_3$ (1.00 mmol) dissolved in methanol (15 mL) containing penicillamine (3.00 mmol) (L20). Color change from colorless to yellow occurred. Mixture was stirred overnight at room temperature after which any solid was removed by vacuum filtration. Solvent was removed from the resulting filtrate and a yellow oil formed. This was left at 4° C. for several days resulting in a yellow solid. The solid was recrystallized from methanol.

6.1.12 Synthesis of Complex 21

$Bi(NO_3)_3 \cdot 5H_2O$ (0.50 mmol) and N-acetyl-L-cysteine (1.50 mmol) (L21) were dissolved in deionized water (15 mL) and left to stir at room temperature for 1 hour. NaOH (3 mL, 1 M) was added to the resulting yellow solution to raise the pH to around 6. The solution was then filtered to remove any insoluble impurities and then rotary evaporated to remove the water. The solid product was then washed with ethanol and vacuum filtered to remove extra $NaNO_3$.

Complex 6 (bismuth subsalicylate) and complex 14 (bismuth subgallate) were purchased from Alfa Aesar. Complex 10 (colloidal bismuth subcitrate, CBS) and ranitidine bismuth citrate (RBC) were kindly provided by Livzon Pharmaceutical Group. The characteristic information of these exemplary is shown in Table 1.

TABLE 2

| MBL | Compounds | $IC_{50}$ (μM) |
|---|---|---|
| NDM-1 | 10 (CBS) | 5.83 ± 0.53 |
|  | 12 | 3.86 ± 0.95 |
|  | 21 | 17.69 ± 0.98 |
|  | $Bi(NO_3)_3$ | 1.89 ± 0.23 |
| VIM-2 | 10 (CBS) | 44.45 ± 3.94 |
|  | 15 | 6.17 ± 0.35 |
|  | $Bi(NO_3)_3$ | 2.45 ± 0.63 |

TABLE 3

| Compound | $K_m$ | $V_{max}$ |
|---|---|---|
| — | 53.7 ± 9.5 | 0.85 ± 0.04 |
| 10 (CBS) | 22.3 ± 5.4 | 0.26 ± 0.01 |

6.2 Example 2: Cytotoxicity of Exemplary Bi(III) Complexes

6.2.1 XTT Assay

Figure 1:
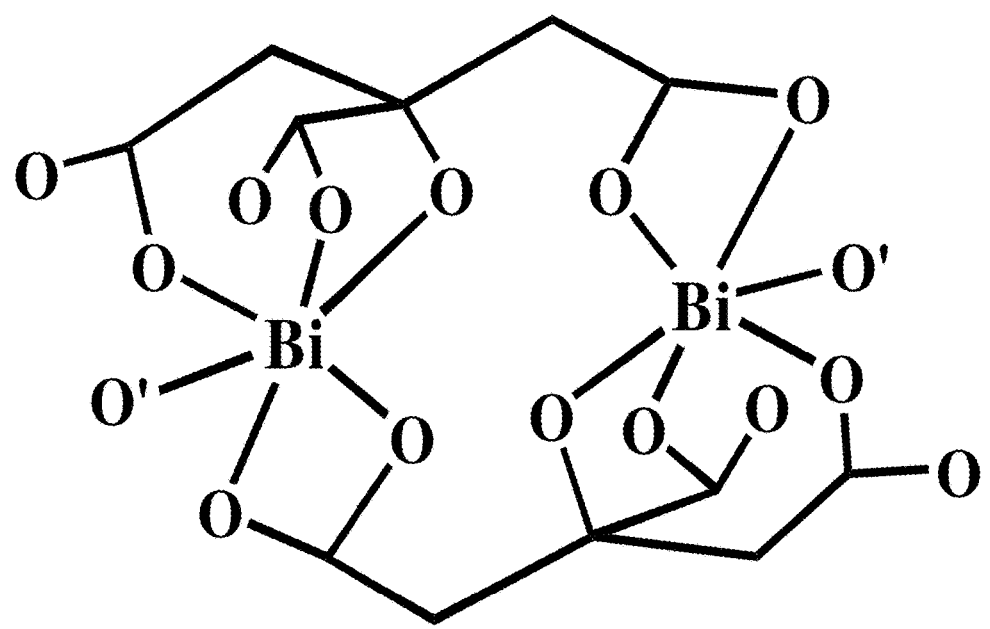
FIG. 1 shows the basic dimeric unit of exemplary clinically used bismuth compounds, colloidal bismuth subcitrate (CBS).
Figure 2:
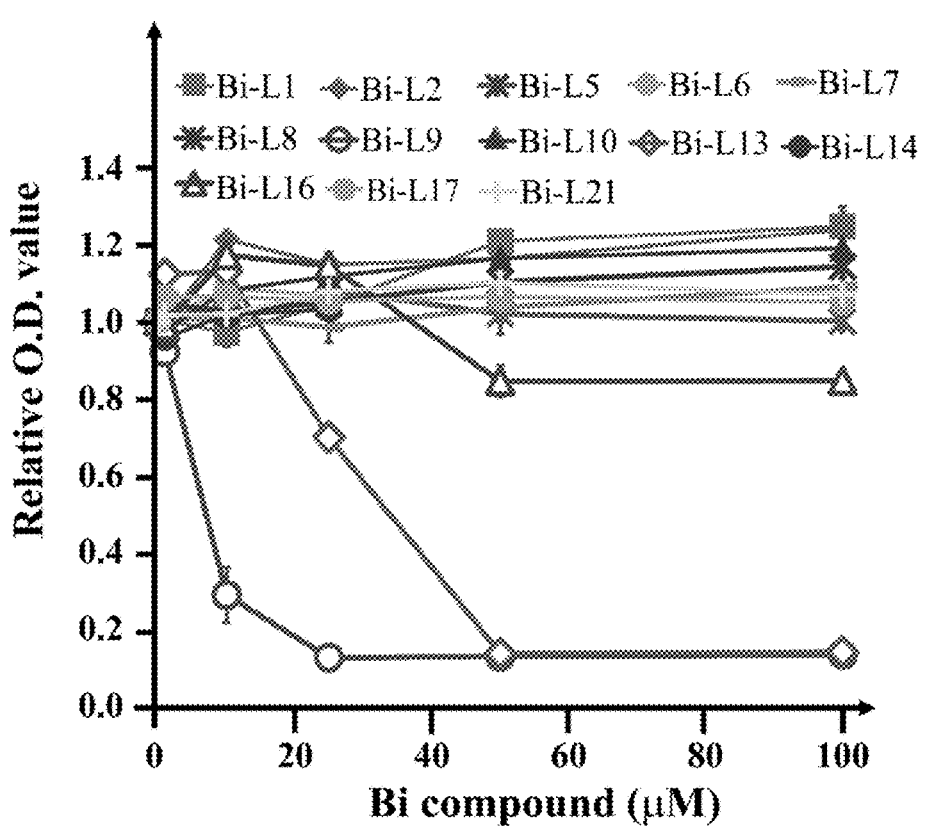
FIG. 2 shows the cell viability test by XTT assay upon treatment of human liver cells (MIHA) with different amounts of Bi(III) compounds.
Figure 3:
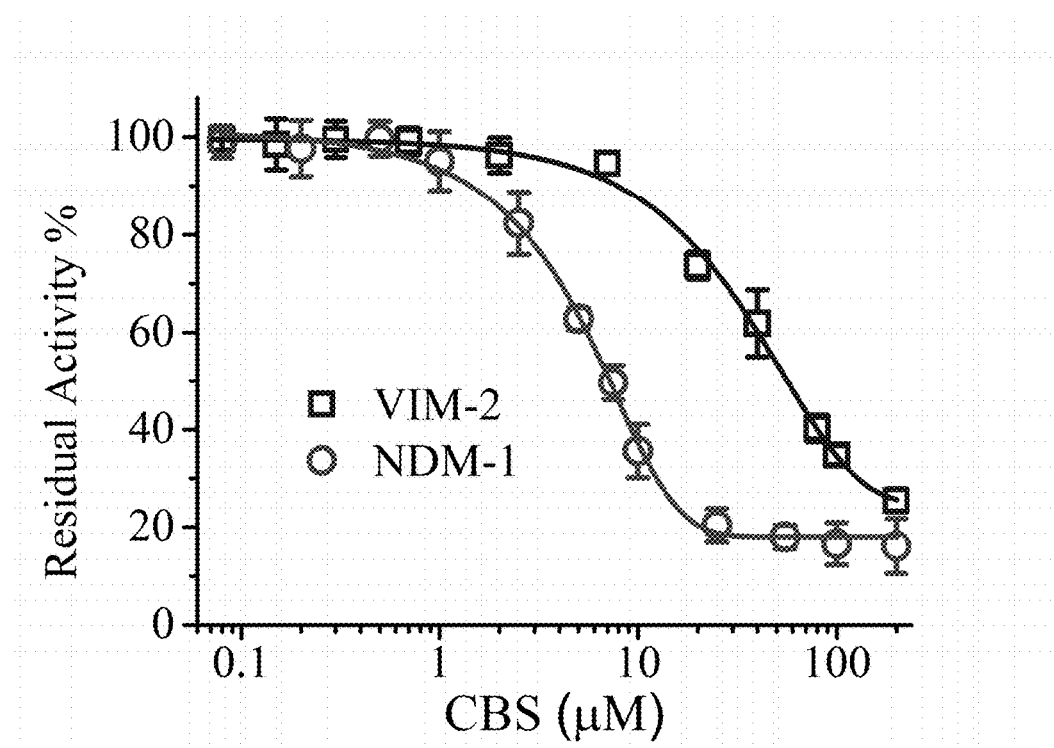
FIG. 3 shows the inhibition of enzymatic activity of purified NDM-1 and VIM-2 by CBS with $IC_{50}$ values of 5.83 μM and 44.45 μM respectively.
Figure 4:
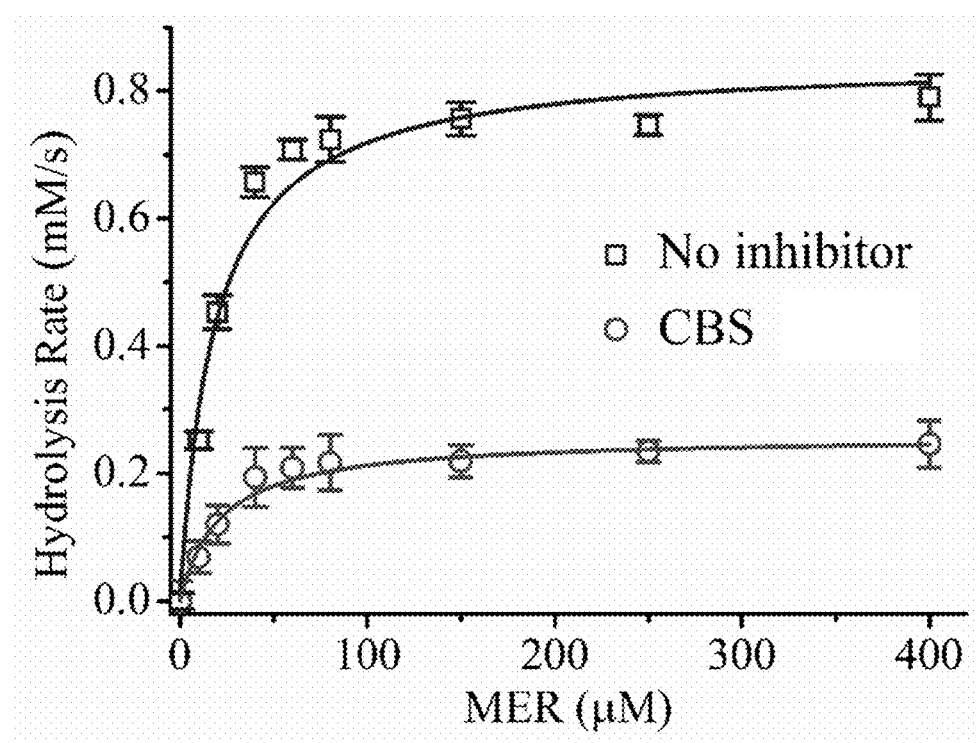
FIG. 4 shows the comparison of the hydrolysis rates of meropenem (MER) by native NDM-1 and Bi-bound NDM-1 (Bi-NDM-1). The corresponding $V_{max}$ and $K_m$ values are summarized in Table 3
Figure 5:
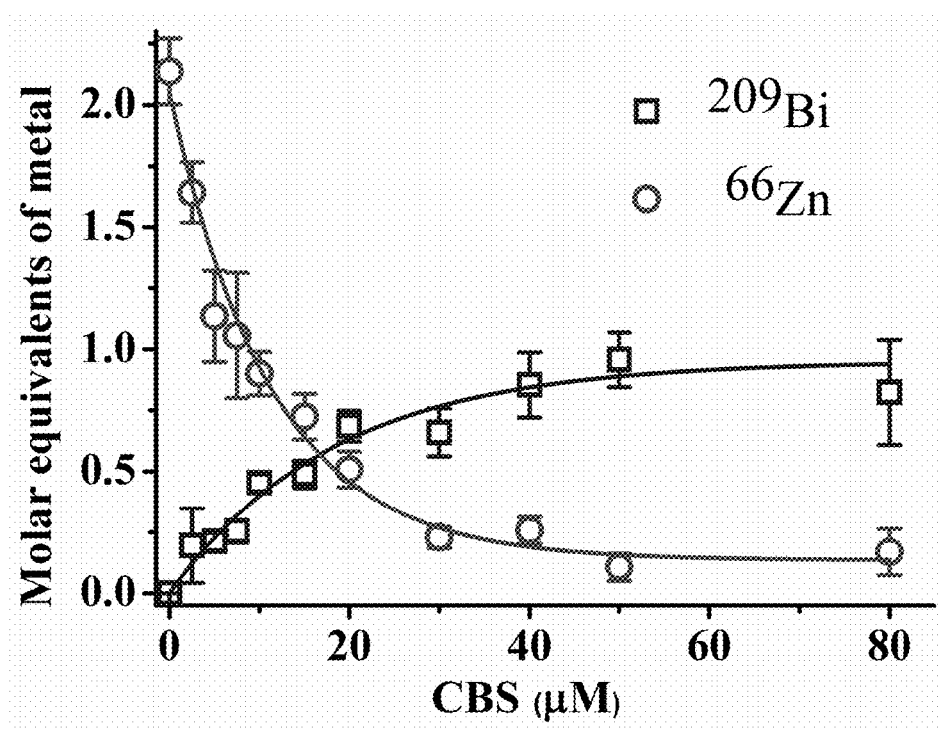
FIG. 5 shows the substitution of Zn(II) in NDM-1 by Bi(III) as determined by ICP-MS. With addition of increasing amounts of CBS to the native NDM-1 samples, Zn(II) was gradually released and binding of one molar equivalent of Bi(III) led to two molar equivalents of Zn(II) to be replaced from NDM-1.
Figure 6:
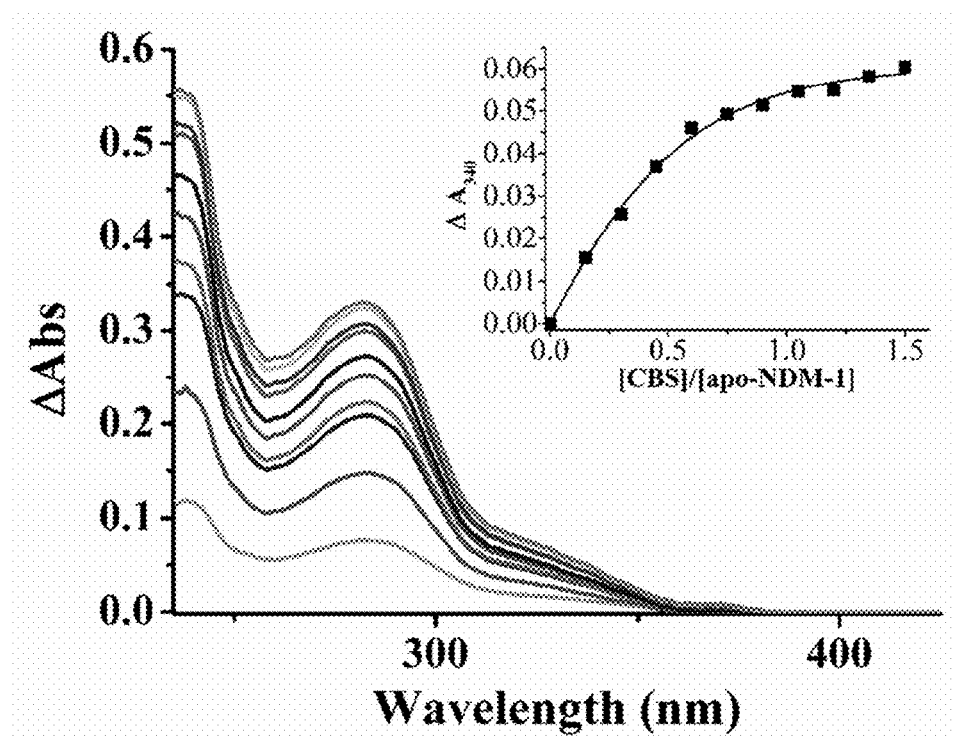
FIG. 6 shows different UV-vis spectra of apo-NDM-1 upon addition of 0.2 to 1.5 molar equivalents of Bi(III). The inset shows the changes of absorbance at 340 nm.

The growth and viability characteristics from the effect of bismuth on MIHA cells were measured using the cell proliferation kit II XTT assay (Roche Diagnostics, USA), according to the manufacturer's instruction. $1-2 \times 10^4$ cells/well were grown in flat-bottom 96-well plates (Costar, Corning Incorporated, NY, USA) in a final volume of 100 μl culture medium per well for an overnight. Cells were then exposed to bismuth compounds (1 to 100 μM) for 2 days. Those grown under culture medium alone were used as a negative control. After a fixed incubation duration, 50 μl of XTT labeling mixture was added to each well, and the cells were incubated for 2 hours at 37° C. under a humidified atmosphere of 5% $CO_2$. The formation of formazan dyes, produced only by metabolic active cells, was detected spectrophotometrically at 490 nm. From the XTT test result shown in FIG. 2, most exemplary bismuth complexes did

TABLE 1

| Complex | Molecular formula | Primary ESI-MS observed (calculated) (m/z) | Assignment (+ve/−ve) | Solubility |
|---|---|---|---|---|
| 1 | $C_{44}H_{28}BiN_4$ | 820.9(821.1) | $[Bi(L1)]^+$ | DMSO |
| 2 | $C_{44}H_{28}BiN_4O_4$ | 885.5 (885.2) | $[Bi(L2)]^+$ | DMSO |
| 3 | $C_{48}H_{36}BiN_4$ | 877.8 (879.3) | $[Bi(L3)]^+$ | DMSO |
| 4 | $C_{48}H_{36}BiN_4O_4$ | 941.8 (943.2) | $[Bi(L4)]^+$ | DMSO |
| 5 | $C_{18}H_{12}BiN_2O_2$ | 496.9 (497.2) | $[Bi(L5)_2]^+$ | 2% HCl |
| 6 | $C_7H_5BiO_4$ | — | — | Insoluble |
| 7 | $C_{14}H_8BiO_4S_2$ | 513.3(513.3) | $[Bi(L7)_2 + M]^+$ | DMSO |
| 8 | $C_5H_{11}BiNO_4S \cdot NaNO_3$ | 473.6 (474.2) | $[Bi(L8)(OH)_2 + NaNO_3]^+$ | DMSO |
| 9 | $C_{12}H_{10}BiN_2O_4$ | 459.2 (459.9) | $[Bi(L9)_2 + 2H]^+$ | DMSO |
| 10 | $C_{12}H_8KBi_2O_{14}$ | 833.3 (833.3) | $[Bi2(L10)_2 + K]^-$ | $H_2O$ |
| 11 | $C_6H_6BiNO_6 \cdot 2H_2O$ | 432.6 (432.1) | $[Bi(L11)(H_2O)_2 - 4H]^-$ | $H_2O$ |
| 12 | Bi-EDTA | — | — | $H_2O$ |
| 13 | $C_{12}BiO_4Br_8$ | 1057.1 (1056.3) | $[Bi(L13)_2]^-$ | DMSO |
| 14 | $C_7H_5BiO_6$ | — | — | Insoluble |
| 15 | $C_{18}H_{26}Bi_2N_2O_6S_2 \cdot KCl$ | 922.4 (923.1) | $[Bi(L15)_2 + KCl]^+$ | DMSO |
| 16 | $C_{20}H_{16}BiN_6O_6$ | 645.1 (645.3) | $[Bi(L16)_2(NO_3)_2]^+$ | DMSO |
| 17 | $C_{10}H_{15}BiN_3O_6S$ | 512.1(512.1) | $[Bi(L17)-2H]^-$ | $H_2O$ |
| 18 | $C_6H_{12}BiN_3O_6$ | 430.9 (431.2) | $[Bi(L18)_3]^+$ | $H_2O$ |
| 19 | $C_9H_{18}BiN_3O_9Cl_2$ | 593.0 (592.1) | $[Bi(L19)_3]^+$ | DMSO |
| 20 | $C_5H_{10}BiNO_4S \cdot NaNO_3$ | 473.6 (474.2) | $[Bi(L20)(OH)_2 + NaNO_3]^+$ | DMSO |
| 21 | $C_{15}H_{27}BiN_3O_9S_3 \cdot NaNO_3$ | 784.1 (783.5) | $[Bi(L21)_3 + (NaNO_3)_3]^+$ | $H_2O$ |
| RBC | — | — | — | $H_2O$ | not exhibit or showed very low cytotoxicity against MIHA cells even at 100 μM (the highest dose test) except for 9 and 13.

6.3 Example 3: In Vitro Mechanistic Studies of Enzyme Inhibition

6.3.1 Construction of Wild-Type NDM-1 and VIM-2 Expression Vector

Full length NDM-1 protein comprises an N-terminal signal peptide (Met1-Pro28) for directing the protein to the periplasm of bacteria after protein translation and was subsequently cleaved during protein maturation process. The wild type expression vectors pET-28a-NDM-1 and pET-28a-VIM-2 were generated as described below. Polymerase chain reaction (PCR) was performed using KOD Hot Start DNA Polymerase (Novagen). The synthesized primer pair "NDM-1_29-270_WT_for/NDM-1_29-270_WT_rev" or "VIM-2_21-226_WT_for/VIM-2_21-226_WT_rev" (Life Technologies) was respectively used for amplifying the gene encoding NDM-1 protein (Gly29-Arg270) or VIM-2 protein (Ser21-Glu266). As a result, NdeI and EcoRI restriction sites were incorporated at the 5' and 3' end of the amplified NDM-1 and VIM-2 gene respectively. The NDM-1 and VIM-2 gene were then respectively inserted into plasmid pET-28a(+) (Novagen) in between the NdeI and EcoRI site so that an N-terminal His-tag was engineered, facilitating protein purification by nickel affinity chromatography. The plasmid construct with the correct insert was subsequently transformed into E. coli XL-1 Blue (Life Technologies) for cloning. The plasmid pET-28a(+) bearing the kanamycin-resistance gene was selected to avoid contamination of other β-lactamases with NDM-1 or VIM-2. All plasmid constructs of variants were transformed into E. coli XL-1 Blue (Life Technologies) for cloning. The DNA sequences of the constructs were confirmed by DNA sequencing.

PCR primers for expressing NDM-1(29-270) and VIM-2_(21-266):

```
NDM-1_29-270_for:
GGGGGCATATGGGTGAAATCCGTCCGAC

NDM-1_29-270_rev:
GGGGGGAATTCTTAACGCAGTTTATCAGCCAT

VIM-2_21-266_for:
GGGGGCATATGAGCCCGCTGGCGTTTAGCGTG

VIM-2_21-266_rev:
GGGGGGAATTCCACCACGCTGCGGTTGGTATG
```

6.3.2 Purification of Wild-Type NDM-1 and VIM-2

Wild-type NDM-1 or VIM-2 expression vector was subsequently transformed into E. coli BL21(DE3) for protein expression. Fresh colony was picked and inoculated in 1 L Luria-Broth medium supplied with 50 μg mL$^{-1}$ kanamycin at 37° C. until O.D. reaches 0.6. After the addition of 0.2 mM isopropyl β-D-1-thiogalactopyranoside and 0.2 mM ZnSO$_4$, the cells were induced to overexpress NDM-1 at 25° C. for 16-18 hrs. To purify the wild-type NDM-1 or VIM-2, cultured cells were harvested and lysed by sonication in a lysis buffer [20 mM HEPES/Na pH 7.0, 0.5 M NaCl and 1 mM phenylmethanesulfonyl fluoride (PMSF)]. The lysate was then centrifuged at 20,000 g for 30 mins to remove most of the insoluble cell debris. The supernatant was subsequently filtered using 0.45 μm filter (Sartorius) and loaded onto a Ni$^{2+}$-NTA affinity chromatography column (GE Healthcare) at a rate of 2 mL min$^{-1}$. The column was washed using 5× column volume of washing buffer [20 mM HEPES, pH 7.0, 500 mM NaCl and 30 mM imidazole] and the protein was eluted out using 4× column volume of elution buffer [20 mM HEPES, pH 7.0, 500 mM NaCl and 300 mM imidazole]. The N-terminal His-tag was cleaved by thrombin digestion at 25° C. for 3 hrs using the cleavage buffer [20 mM HEPES/Na pH 7.0, 150 mM NaCl] and the fusion His-tag was separated from NDM-1 by passing through the Ni$^{2+}$-NTA column again using washing buffer so that majority of the NDM-1 protein was in the flow-through fraction. The proteins were further purified in purifying buffer [20 mM HEPES, pH 7.0, 150 mM NaCl] using HiLoad 16/60 Superdex 200 pg gel filtration column to a purity of >98%, judging from SDS-PAGE gel. The proteins were concentrated using Amicon Ultra-15 Centrifugal Filter Devices (Millipore) and was separated into aliquots in storage buffer [50 mM HEPES/Na pH 7.0] for storage at −20° C. The protein concentration was determined by using bicinchoninic acid protein assay kit (Novagen) and the yield of the purified NDM-1 was estimated to be 0.23 mg L$^{-1}$ of LB medium. Purified NDM-1 and VIM-2 were determined by ICP-MS to contain approximately 2 molar equivalents of Zn(II) (i.e. Zn$_2$-NDM-1) after the series of purification steps.

6.3.3 IC$_{50}$ Enzyme Inhibition Assay

Freshly prepared Zn$_2$-NDM-1 (50 nM) or Zn$_2$-VIM-2 were first incubated with various concentrations of Bi(III) compounds for 1 h at 25° C. The assay was performed in a 1 cm quartz cuvette using the kinetic mode of Varian Cary® 50 UV-visible spectrophotometer at 25° C. The final assay buffer contains 50 mM HEPES/Na pH 7.0, 100 mM NaCl and 100 μM MER. The decrease in absorbance at 300 nm due to ring-opening of MER was monitored every second for a duration of 10 mins until the reaction was completed. The initial rate were extracted and calculated from each reaction curves. Half maximum inhibitory concentrations (IC$_{50}$) of CBS to NDM-1 and VIM-2 were determined to be 5.83±0.53 μM and 44.45±3.94 μM respectively.

6.3.4 Zn(II) Supplementation Assay

Figure 7:
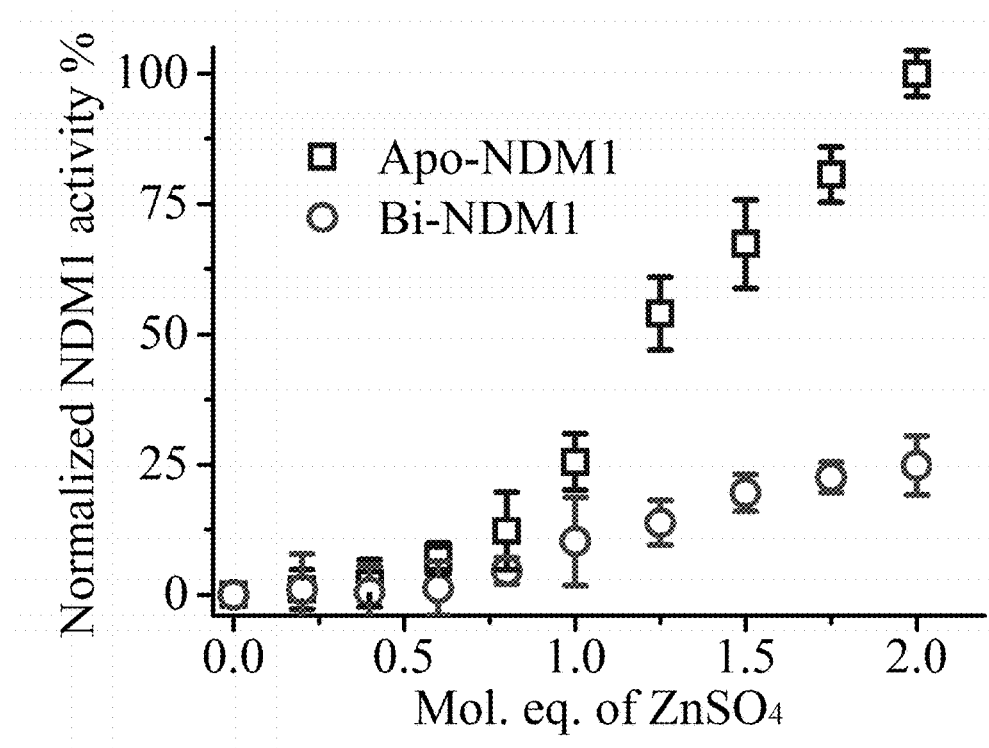
FIG. 7 shows the comparison of the enzyme activities of apo-NDM-1 and Bi-NDM-1 upon supplementation of various concentrations of $ZnSO_4$.

To investigate whether enzyme inhibition can be reversed, enzyme activities of apo-NDM-1 and Bi-NDM-1 were compared with the supplementation of Zn(II). Bi-NDM-1 (50 nM) was prepared by pre-incubation of apo-NDM-1 with CBS for 2 h at 25° C. and the bound Bi was verified using ICP-MS. The above protein solutions were mixed with ZnSO$_4$ at concentration up to 2 molar equivalents to NDM-1 and 100 μM MER. The change in absorbance at 300 nm was monitored in a 1 cm quartz cuvette using Varian Cary® 50 UV-visible spectrophotometer at 25° C. for reaction rate calculations. Reaction rate of apo-NDM-1 with addition of 2 molar equivalents of ZnSO$_4$ was normalized to be 1. It was found that upon supplementation of Zn(II) to Bi-NDM-1 solution, the enzyme activity can only be restored to 25%. In contrast, the enzyme activity can be recovered significantly upon the supplementation of Zn(II) to apo-NDM-1 (FIG. 7). This undoubtedly suggests that Bi(III) inhibits NDM-1 irreversibly and Zn(II) cannot reoccupy the active site to recover its enzyme activity after Bi(III) binding. To confirm this, the metal contents of both Zn(II) and Bi(III) were monitored by inductively-coupled plasma mass spectrometry (ICP-MS) as described below.

6.3.5 Monitoring Zn(II) Displacement by Bi(III) Using ICP-Mass Spectrometry (ICP-MS)

To monitor the replacement of Zn(II) by Bi(III), inductively-coupled plasma mass spectrometry (ICP-MS) was employed to accurately quantify $^{209}$Bi and $^{66}$Zn contents in various purified NDM-1 samples. Purified $Zn_2$-NDM-1 was prepared as described previously and was dissolved in trace-metal-free ICP-MS buffer containing 50 mM HEPES, pH 7.0 through cycles of buffer washing using an Amicon Ultra-15 Centrifugal Filter Devices with 3 kDa cut-off. $Zn_2$-NDM-1 (20 μM) was incubated with various concentrations of CBS at 25° C. for 5 hrs with mild shaking. The samples were subsequently dialyzed in ICP-MS buffer to remove unbound-metal ions and were acidified with 10% (v/v) nitric acid for 1 h with gentle heating for releasing the bound metal ions from the protein for ICP analysis. The samples were then mixed with 115In as an internal standard to reach a final concentration of 10 ppb in 1% $HNO_3$. After calibration with the isotope standards $^{209}$Bi, $^{66}$Zn and $^{34}$S from Sigma, the samples were subsequently injected into a quadrupole-based inductively coupled plasma mass spectrometer (Agilent 7500a, Agilent Technologies, CA, USA). $^{209}$Bi, $^{66}$Zn and $^{34}$S isotopes abundances were determined simultaneously by integration of peak areas using the build-in software from the instrument so that $^{34}$S abundance serves as a way for quantifying protein concentration in each sample. It was found that 2.13 molar equivalents of Zn(II) were replaced by 0.96 equivalent of Bi(III) as determined from the respective metal contents of the sample, providing direct evidence for competitive binding of Bi(III) to the protein.

6.3.6 UV-vis Spectroscopy

UV-vis spectra were collected on a Varian Cary 50 spectrophotometer using a 1-cm quartz cuvette at 25° C. Freshly prepared apo-NDM-1 sample (50 μM) in 20 mM HEPES buffer containing 50 mM NaCl at pH 7.4 was prepared and aliquots of bismuth solution were gradually titrated into the sample. Binding of Bi(III) to apo-NDM-1 was monitored by measurement of the increase in absorption at approximately 340 nm due to ligand-to-metal-charge transfer (LMCT) involving cysteine residue. Since Cys208 is the only cysteine residue in the protein, LMCT involving cysteine residue provides solid evidence for Bi(III) binding to Cys208 and subsequently leading to the dissociation of Zn(II) from NDM-1. To further prove our hypothesis, X-ray crystallographic studies were carried out as mentioned in Example 4 below.

6.4 Example 4: Crystallographic Studies of Bismuth Binding to NDM-1

6.4.1 Crystallization, Diffraction Data Collection and Structure Determination Crystals of native NDM-1 were obtained through hanging-drop vapor diffusion method. Briefly, NDM-1 protein (concentrated to 100 mg mL-1) was mixed with the precipitant containing 0.1 M Bis-Tris at pH 5.5, PEG 3350 15% (w/v) and 20 mM L-proline in equal volume ratio. Under this condition, crystals in P1 space group with eight molecules in one asymmetric unit could be obtained easily and they diffracted to resolution of 1.8 to 2.0 Å. After fishing up the P1 crystals, new crystals in space group of P21 were grown by chance and they generally have greater diffraction limit to resolutions of 0.93~1.0 Å. The P21 crystals were used as seeds for later crystallization of NDM-1. Diamond-like or rectangular crystals appeared within a day after seeding and grew up to full size in three days to a week.

To obtain the bismuth bound crystals, zinc ions in the native crystals were extracted and bismuth compounds were soaked into these crystals. Briefly, native crystals were crosslinked with 25% glutaraldehyde at 25° C. for 30 min and then soaked in chelating solution (0.1 M sodium acetate pH 4.6, 25% PEG 3350, 20% glycerol, 10 mM EDTA) for an overnight. The crystals were washed three times in cryo-protectant solution (0.1 M Bis-Tris pH 5.5, 25% PEG 3350, 20% glycerol). Soaking was done in the soaking solution containing 0.1 M Bis-Tris (pH 5.5), 25% PEG 3350, 20% glycerol, 5 mM TCEP and 1 mM Bi(III) gluconate for 17 hrs. The crystals were then washed with the cryo-protectant solution for four times and flash frozen into liquid nitrogen.

The diffraction data were collected at BL17U at the Shanghai Synchrotron Radiation Facility. Two data sets were collected at wavelengths of 0.92 and 0.93 Å, which crossed the absorption edge of elemental bismuth. Excitation scan was performed for each crystals to confirm that zinc ions were completely extracted out and only bismuth was left in the crystals. The diffraction data were processed with HKL2000. Molecular replacement was performed using the program Phaser from CCP4 suit and the ampicillin-bound NDM-1 (PDB code: 3Q6X) was used as a searching model. Models were refined with Refmac and cycled with manual rebuilding in Coot. Anomalous data were used in refinement and the anomalous signal strength was compared between the two data sets collected at wavelength of 0.92 and 0.93 Å.

The anomalous peak for data collected at 0.92 Å was at least two-fold higher than that of data collected at 0.93 Å. Together with the excitation scan, we confirmed that the anomalous signal was contributed by bismuth. The occupancy of bismuth was refined according to the strength of anomalous signal at early refinement and assessed by B-factor in later stages. TLS refinement was incorporated into later refinement processes. Solvents were added automatically in Coot and then manually inspected and modified. The final models were analyzed with MolProbity. Data collection and model refinement statistics are summarized in Table 4.

TABLE 4

| Data collection | Bi(III)-gluconate |
|---|---|
| Space group | P21 |
| Cell dimensions | |
| a, b, c (Å) | 41.60, 60.18, 41.80 |
| α, β, γ(°) | 90, 98.95, 90 |
| Resolution (Å) | 50~1.55(1.61~1.55) |
| Unique reflections | 27612(2309) |
| Completeness (%) | 95.5(94.2) |
| Redundancy | 7.0(6.9) |
| Wilson B-factor | 12.79 |
| Rmerge | 0.116(0.697) |
| I/σI | 18.1(3.1) |
| Refinement | |
| Resolution (Å) | 50~1.55 |
| Rwork | 0.1627(0.2194) |
| Rfree | 0.1935(0.2502) |
| No. atoms | 1951 |

TABLE 4-continued

| Data collection | Bi(III)-gluconate |
|---|---|
| Protein | 1737 |
| Bi | 1* |
| Water | 206 |
| Protein residues | 228 |
| Ramachandran plot | |
| Favored (%) | 99 |
| Outliers (%) | 0 |
| Average B-factors | 19.62 |
| Protein | 17.90 |
| Water | 33.77 |
| Bia/Bib | 14.94/18.42 |
| Occupancy of Bia/Bib | 0.55/0.10 |
| R.m.s. deviations | |
| Bond lengths (Å) | 1.37 |
| Bond angles (°) | 0.010 |

6.5 Example 5: In Vitro Antimicrobial Activity Assessment

The anti-resistance activity of bismuth compounds was examined against MBL producing bacteria strains. The method involved cell-based minimum inhibitory concentration (MIC) and minimum bactericidal concentration (MBC) assay, time-kill assay and in vitro cell infection assay.

6.5.1 Bacteria

The bacteria employed involved E. coli ATCC 25922, E. coli clinical isolate (NDM-1$^+$), E. coli (NDM-1-), K. pneumonia clinical isolate (NDM-1$^+$), C. freundii clinical isolate (NDM-1$^+$), E. coli clinical isolate (IMP-4$^+$), E. coli BL21 (VIM-2$^+$) and Rosetta (NDM-1$^+$). K. pneumonia clinical isolate (NDM-1$^+$) and C. freundii clinical isolate (NDM-1$^+$) were kindly given by Prof. Woo, Patrick Chiu Yat (LKS Faculty of Medicine, HKU). E. coli clinical isolate (IMP-4$^+$) were kindly given by Prof. Ho, Pak Leung (LKS Faculty of Medicine, HKU). E. coli (NDM-1) was screened by 20$^{th}$ generation serial passages of E. coli clinical isolate (NDM-1$^+$) in antibiotic-free medium. The missing of NDM-1 gene was confirmed by PCR check.

6.5.2 Microdilution MIC and MBC Assay

Both MIC and MBC assay were used to quantitatively evaluate the antimicrobial activity over the combination of MER and Bi(III) compounds or pharmaceutically acceptable salts thereof. Fractional inhibitory concentration index (FICI) was used to mirror the synergism between them.

MIC values of either antibiotics or Bi(III) compounds were determined firstly by standard broth micro-dilution method (Clinical and Laboratory Standards Institute (CLSI) M100-S20, 2010). Briefly, bacteria cells were cultured in LB broth overnight at 37° C. at 250 rpm and the optical density was measured at 600 nm ($OD_{600}$) using a microtiter plate reader. The bacteria density was adjusted to about $1 \times 10^6$ CFU mL$^{-1}$ and checked by CFU counting on agar plates afterwards. Tested compounds were added triplicately into individual wells of flat-bottomed 96-well plates and performed two-fold serial dilution, followed by addition of prepared bacterial inoculum. The plate was then incubated at 37° C. overnight. Lanes with no antibiotics or bismuth compounds served as positive controls and lanes with no bacteria added served as negative controls. The MIC was determined as the lowest concentration of compounds that could inhibit the growth of microorganism by both visual reading and $OD_{600}$ measurement. At the end of MIC assay, a 50 µL aliquot of each well (containing a specified antimicrobial concentration) for each isolate tested was applied to a LB agar plate and incubated at 37° C. in ambient air overnight. Resulting growth (or lack of growth) was examined after overnight culturing and the lowest concentration that inhibits 99.9% of the original culture was taken as MBC.

For the test of drug combination, antibiotics and Bi(III) compounds were co-administered at concentrations up to 8 times higher than the MIC of the compounds tested alone. Other procedures and the check of MIC were kept strictly the same. The FICIs were determined based on the following equation:

$$FICI = FICA + FICB = C_A/MIC_A + C_B/MIC_B$$

where MICA and MICB are the MIC values of compound A and B when functioning alone, and $C_A$ and $C_B$ are the concentrations of compound A and B at the effective combinations. Synergism was defined as FICI≤0.5, indifference was defined as FICI>0.5 and <4, and antagonism was defined as FICI≥4. All of the determinations were performed at least in triplicate on different days.

Using the methods described above, exemplary Bi(III) compounds were evaluated for their ability to kill or inhibit the growth of MBL producing bacteria in the combination with MER. FIG. 10(a) shows the heat map of checkerboard MIC on the combination of MER and CBS against NDM-1 producing E. coli. When used alone, MER had relatively high MIC values, often greater than 16 µg mL$^{-1}$, which are far beyond the empirical susceptible level for Enterobacteriaceae (2 µg mL$^{-1}$). As the concentration of CBS escalated, MIC of MER was gradually lowed to 2 µg mL$^{-1}$ and FIC index was calculated to be 0.250, indicative of synergistic effect between them. In contrast, no inhibition was observed when NDM-1-null E. coli stain was used (FIG. 10(b)). Such a synergy was also found between MER and other exemplary Bi(III) compounds against other NDM-1-producing bacterial stains and other MBL-producing bacterial stains as summarized in Table 5, 6 and 7. Upon the combination with tested Bi(III) compounds, MICs of MER were substantially lowered, typically by 4~32-folds against MBL-producing bacteria. The representative results preliminarily indicate the synergism between the MER and tested Bi(III) compounds, which might contribute from the inhibition of MBL produced by the tested bacterial pathogens, consistent with the previously described enzymatic study in Example 3.

TABLE 5

| Strain | Compound | MER with Bi(III) compound at 32 µg mL$^{-1}$ | | FIC Index |
|---|---|---|---|---|
| | | MIC (µg mL$^{-1}$) | MBC (µg mL$^{-1}$) | |
| E. coli (NDM-1$^+$) | — | 16 | 16 | — |
| | 1 | 4 | 8 | 0.266 |
| | 2 | 16 | 16 | 1 |
| | 3 | 8 | 16 | 1 |
| | 4 | 8 | 16 | 1 |
| | 5 | 1 | 4 | 0.187 |
| | 6 (BSS) | 2 | 8 | 0.281 |
| | 7 | 1 | 2 | 0.250 |
| | 8 | 8 | 8 | 0.375 |
| | 9 | 0.5 | 2 | 0.156 |
| | 10 (CBS) | 2 | 4 | 0.250 |
| | 11 | 4 | 8 | 0.375 |
| | 12 | 0.5 | 0.5 | 0.094 |

TABLE 5-continued

| | | MER with Bi(III) compound at 32 µg mL$^{-1}$ | | FIC |
|---|---|---|---|---|
| Strain | Compound | MIC (µg mL$^{-1}$) | MBC (µg mL$^{-1}$) | Index |
| | 13 | 1 | 2 | 0.250 |
| | 14 (BSG) | 4 | 8 | 0.375 |
| | 15 | 0.5 | 0.5 | 0.125 |
| | 16 | 2 | 8 | 0.375 |
| | 17 | 2 | 4 | 0.250 |
| | 18 | 8 | 16 | 1 |
| | 19 | 2 | 2 | 0.375 |
| | 20 | 2 | 2 | 0.313 |
| | 21 | 0.5 | 1 | 0.188 |
| | RBC | 2 | 4 | 0.250 |
| | Bi(NO3)3 | 2 | 4 | 0.266 |

TABLE 6

| | | MER with Bi(III) compound at 32 µg mL$^{-1}$ | | FIC |
|---|---|---|---|---|
| Strain | Compound | MIC (µg mL-1) | MBC (µg mL-1) | Index |
| K. pneumonia (NDM-1$^+$) | — | 16 | 16 | — |
| | 1 | 4 | 16 | 0.375 |
| | 10 (CBS) | 4 | 8 | 0.375 |
| | 21 | 1 | 2 | 0.188 |
| | Bi(NO$_3$)$_3$ | 1 | 1 | 0.125 |
| C. feudii (NDM-1$^+$) | — | 8 | 8 | — |
| | 10 (CBS) | 0.5 | 1 | 0.125 |
| | 21 | 0.5 | 0.5 | 0.188 |
| | Bi(NO$_3$)$_3$ | 2 | 4 | 0.375 |

TABLE 7

| | | MER with Bi(III) compound at 32 µg mL-1 | | FIC |
|---|---|---|---|---|
| Strain | Compound | MIC (µg mL-1) | MBC (µg mL-1) | Index |
| E. coli (VIM-2$^+$) | — | 32 | 32 | — |
| | 10 (CBS) | 0.5 | 1 | 0.047 |
| | 21 | 0.5 | 1 | 0.063 |
| | Bi(NO$_3$)$_3$ | 1 | 2 | 0.063 |
| E. coli (IMP-4$^+$) | — | 8 | 16 | — |
| | 10 (CBS) | 4 | 8 | 0.313 |
| | 21 | 2 | 2 | 0.250 |
| | Bi(NO$_3$)$_3$ | 4 | 8 | 0.313 |

TABLE 8

| | | MER with CBS (mg mL$^{-1}$) at | | | |
|---|---|---|---|---|---|
| Mic multiple | MER | 32 | 64 | 128 | 256 |
| 0.5 | >1.31 × 10$^{-7}$ | >5.22 × 10$^{-8}$ | 1.23 × 10$^{-8}$ | 9.84 × 10$^{-10}$ | 1.31 × 10$^{-9}$ |
| 1 | >4.92 × 10$^{-8}$ | 4.10 × 10$^{-8}$ | 1.15 × 10$^{-9}$ | — | — |
| 2 | 3.62 × 10$^{-8}$ | 3.28 × 10$^{-9}$ | — | | |
| 4 | 4.43 × 10$^{-8}$ | — | | | |
| 8 | 3.12 × 10$^{-8}$ | | | | |
| 16 | — | | | | |
| 32 | | | | | |
| 64 | | | | | |

The antibacterial activities of CBS with other β-lactam antibiotics were shown in FIG. 11. Although none of the test combinations totally inhibited the growth of bacteria, the growth rate was evidently lowered in Rosetta (DE3) (NDM-1$^+$) bacterial cells by AMOX, ampicillin (AMP), nafcillin (NAF) and cefdinir (CEF) in the presence of bismuth complexes. AMOX, NAF and CEF becomes potent upon addition of compound (CPD) 21 with the growth rates of the bacterial cells to be reduced by 77.9%, 60.5% and 61.1%, respectively, while CEF became extremely potent when CBS was used in combination and could reduce the growth rate by 76%. This study demonstrates the in vitro potency of the combination of bismuth compounds with other antibiotics against NDM-1-producing bacteria.

6.5.3 Time Kill Assay

Time kill assay was used to further explore the synergy between MER and Bi(III) compounds which were represented by CBS herein. In a typical assay, the concentrations of the compounds used in this test represent as follows: 16 µg mL$^{-1}$ MER, 32 µg mL–1 CBS. Bacteria were cultured for overnight and diluted 1:250 into LB broth at 37° C. for 3 hrs to reach log phase. The initial bacterial concentration was adjusted to ~10$^7$ CFU mL$^{-1}$ according to standard curve. Tested compounds either alone or in combination was added to 20 mL of freshly prepared bacterial solution in a 50 ml tube, and incubate at 37° C. LB broth with no compounds served as a positive control. Aliquots of 100 mL suspension were withdrawn after different time intervals (0, 1, 2, 4, 6, 8, and 24 hrs). Bacterial concentrations were estimated from colony counts by serial dilution in phosphate-buffered saline (PBS) and plating on LB agar. All assays were triplicated and performed three times in different days. Data from three independent experiments were averaged and plotted as log$_{10}$ CFU mL$^{-1}$ versus time (h) for each time point over 24 hrs as shown in FIG. 12.

In comparison to single components, bacteria density was significantly lowered by more than 1000-fold when exposed to the compound combination of CBS and MER at the endpoint of the assay. According to NCCLS, this indicates an evident synergism between CBS and MER and the bactericidal effect over the compound combination was observed as well.

6.5.4 Resistance Study

Given the very notion of MIC, all susceptible bacterial cells will be suppressed or killed by a dose above it. However, bacterial population is often large; an infection will likely contain first-step mutants with lowed susceptibility. Thus, the dose of compounds at MIC will adversely amplify the population of those less-susceptible mutants.[26] Thus mutant prevention concentration (MPC), defined as a compound concentration that suppresses the growth of first-step resistant mutant in large quantity of susceptible bacterial population, together with mutant prevention index (MPI=MPC/MIC), is introduced to estimate the mutant prevention ability of exemplary compound combination.

For a typical test, *E. coli* cells (NDM⁺) at 1~2×10$^{10}$ CFU were spread onto LB agar containing combinations of MER and CBS at identical concentrations. All the plates were incubated at 37° C. Upon incubation for 48 hrs, up to 4 colonies were picked and re-cultured from any plates with observable colonies, followed by the measurement of their MIC values. Any MICs of MER that were higher than the original values (16 µg mL$^{-1}$) were determined as mutant colony. The concentration that restricted the growth of mutant colonies was determined as MPC.

A heat map visualized the degree of mutation frequency (FIG. 13), mutant colonies were still observable even when a high dose (8×MIC) of MER was applied. In contrast, with the increase in CBS dose, the mutation frequency declined significantly as shown in Table 7. The MPI of MER was lowered to 1 and no mutant colony was observable when ≥128 µg mL$^{-1}$ CBS was used. This may contribute from multiple targets mechanism by using bismuth compounds, which is believed as a typical feature of metalloagents. This unique character might play a vital role in endowing the potency of Bi compounds to cope with resistance issue.

6.5.5 In Vitro Cell Infection Assay

To further evaluate the antimicrobial efficacy of CBS in combination with MER, we exploited the in vitro bacterial infection model in mammalian cell. Typically, MDCK cells were cultured in minimum essential Media (MEM) supplemented with fetal bovine serum (FBS, 10%) and grown at 37° C. in the 5% CO$_2$ humidified atmosphere for three days. The MDCK cells were then washed three times with phosphate buffer saline (PBS) solution, liberated with trypsin-EDTA (0.25%) and re-suspended by culture medium. About 500 µL of re-suspended cells were seeded in 24-well plates and incubated as described above for 48 hrs to ensure confluency, resulting in about 1.0×10$^5$ cells per well by typan blue assay. The freshly grown logarithmic *E. coli* (NDM-1⁺) bacterial cells were washed with PBS for three times and re-suspended in MEM/10% FBS. The density was adjusted to 2×10$^7$ CFU mL. Then 500 µL of bacterial suspension was added to each well and substituted for the previous MDCK culture medium. The plates were centrifuged at 800×g for 10 min and then incubated at 37° C. in 5% CO$_2$ for 6 hrs executing the bacteria invasion at multiplicity of infection (MOI) of 200. After the infection, cells were washed with PBS for three times to remove unbound bacteria and refueled with culture medium.

For those cell-invaded bacteria experiments, the infected cells were incubated in culture medium supplemented with 100 µg mL$^{-1}$ ciprofloxacin for 1 h to remove extracellular bacteria. Then the treated cells were washed vigorously with PBS for six times and replenished with culture medium. To measure the initial bacteria density, cells were washed three times in PBS and fully lysed with of 1% Triton X-100 in PBS. The cell lysates were serially diluted and plated on LB agar, and colonies were enumerated by agar plating. For the cell-associated (adherent, internalized and transcytosed) infection, the cells were washed vigorously with PBS for washed six times in the absence of ciprofloxacin treatment. The cell-invaded bacteria herein are defined as those bacteria that penetrate MDCK cells and the cell-associated bacteria are defined as bacteria that penetrate, attach to or transcytose in MDCK cells. After the invasion of bacteria, appropriate concentrations of tested compounds were added to each well in 24-well plates. Cells in the absence of the compounds served as a control. The plates were incubated for overnight at 37° C. Surviving bacteria were enumerated as described previously. The assay was performed in triplicate, repeated three times and the results were expressed as average ±SD.

FIG. 14 shows the CFU reduction of viable bacteria after the treatment with antimicrobial agent. Bacterial loads were at 10$^6$ CFU level even when MER at 2×MIC was used, which however, were dramatically dropped to not greater than 10$^4$ CFU level in the presence of CBS in the cell-associated model. For the cell-invaded model, the compound combination of MER (2×MIC) and CBS was still able to lower the intracellular bacterial density by 9.22 fold compared with mere MER. The studies above demonstrate the in vitro potency of the compound combination of CBS and MER against NDM-1-producing bacteria.

6.6 Example 6: In Vivo Antimicrobial Activity Assessments 6.6.1 Murine Peritonitis Infection The enzyme- and cell-based study with which CBS served to suppress the function of MBLs and boost β-lactam antibiotic activity against MBL producing bacteria demonstrates the potential that current compound combination would exert enhanced antimicrobial efficacy compared with β-lactam antibiotic alone in vivo. To confirm this, a mouse peritonitis model was established and then used for the examination of in vivo compound efficacy.

Briefly, an overnight culture of *E. coli* (NDM-1⁺) was performed 1:250 dilution in 50 mL LB broth and re-grew to about OD of 0.3 in a 250-mL flask after 2.5 hrs shaking at 37° C., 250 rpm. The resulting bacterial pellets were collected and washed by PBS three times for further use. For bacterial infection, mice (female BALB/c strain, 6~8 weeks of age, 18~22 g of weight) were induced intraperitoneally (i.p.) with a dose of 10$^5$ CFU bacteria in a 400 µL aliquot of PBS supplemented with 2% mucin. 4 groups of mice were i.p. administered 4 hrs post-infection with a 100 µL aliquot of PBS, MER, CBS and a combination of MER and CBS, respectively. Body weights and mice survival were monitored for endpoint until day 4 post infection.

The representative results are shown in FIG. 15. The mice became severely diseased 4 hrs post-infection and none of them survived after 20 hrs post-infection. Upon the co-administration with CBS, MER was able to postpone the death of mice and raise the survival rate to 50% comparing with merely 25% by MER itself at the endpoint of experiment.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

REFERENCES (1) Wright, G. D.; Sutherland, A. D. Trends Molecular Medicine 2007, 13, 260.
(2) Fisher, J. F.; Meroueh, S. O.; Mobashery, S. Chemical Reviews 2005, 105, 395.

(3) Medeiros, A. A. Clinical Infectious Diseases 1997, 24, S19.
(4) Walsh, T. R.; Toleman, M. A.; Poirel, L.; Nordmann, P. Clinical Microbiology Reviews 2005, 18, 306.
(5) Feng, H.; Ding, J.; Zhu, D.; Liu, X.; Xu, X.; Zhang, Y.; Zang, S.; Wang, D.-C.; Liu, W. Journal of the American Chemical Society 2014, 136, 14694.
(6) Tripathi, R.; Nair, N. N. ACS Catalysis 2015, 5, 2577.
(7) Cornaglia, G.; Giamarellou, H.; Rossolini, G. M. The Lancet Infectious Diseases 2011, 11, 381.
(8) Munoz-Price, L. S.; Poirel, L.; Bonomo, R. A.; Schwaber, M. J.; Daikos, G. L.; Cormican, M.; Cornaglia, G.; Garau, J.; Gniadkowski, M.; Hayden, M. K.; Kumarasamy, K.; Livermore, D. M.; Maya, J. J.; Nordmann, P.; Patel, J. B.; Paterson, D. L.; Pitout, J.; Villegas, M. V.; Wang, H.; Woodford, N.; Quinn, J. P. The Lancet Infectious Diseases 2013, 13, 785.
(9) Lippmann, N.; Lübbert, C.; Kaiser, T.; Kaisers, U. X.; Rodloff, A. C. The Lancet Infectious Diseases 2014, 14, 271.
(10) Nordmann, P.; Cuzon, G.; Naas, T. The Lancet Infectious Diseases 2009, 9, 228.
(11) Poirel, L.; Nordmann, P. Clinical Microbiology and Infection 2006, 12, 826.
(12) Queenan, A. M.; Bush, K. Clinical Microbiology Reviews 2007, 20, 440.
(13) Woodford, N.; Turton, J. F.; Livermore, D. M. FEMS Microbiology Reviews 2011, 35, 736.
(14) Kumarasamy, K. K.; Toleman, M. A.; Walsh, T. R.; Bagaria, J.; Butt, F.; Balakrishnan, R.; Chaudhary, U.; Doumith, M.; Giske, C. G.; Irfan, S.; Krishnan, P.; Kumar, A. V.; Maharjan, S.; Mushtaq, S.; Noorie, T.; Paterson, D. L.; Pearson, A.; Perry, C.; Pike, R.; Rao, B.; Ray, U.; Sarma, J. B.; Sharma, M.; Sheridan, E.; Thirunarayan, M. A.; Turton, J.; Upadhyay, S.; Warner, M.; Welfare, W.; Livermore, D. M.; Woodford, N. The Lancet Infectious Diseases 2010, 10, 597.
(15) Nordmann, P.; Naas, T.; Poirel, L. Emerging Infectious Diseases 2011, 17, 1791.
(16) Borgia, S.; Lastovetska, O.; Richardson, D.; Eshaghi, A.; Xiong, J.; Chung, C.; Baqi, M.; McGeer, A.; Ricci, G.; Sawicki, R.; Pantelidis, R.; Low, D. E.; Patel, S. N.; Melano, R. G. Clinical Infectious Diseases 2012, 55, e109.
(17) Cantón, R.; Akóva, M.; Carmeli, Y.; Giske, C. G.; Glupczynski, Y.; Gniadkowski, M.; Livermore, D. M.; Miriagou, V.; Naas, T.; Rossolini, G. M.; Samuelsen, Ø.; Seifert, H.; Woodford, N.; Nordmann, P.; the European Network on, C. Clinical Microbiology and Infection 2012, 18, 413.
(18) Shahcheraghi, F.; Nobari, S.; Rahmati Ghezelgeh, F.; Nasiri, S.; Owlia, P.; Nikbin, V. S.; Imani Fooladi, A. A. Microbial Drug Resistance 2012, 19, 30.
(19) Ho, H. J.; Toh, C. Y.; Ang, B.; Krishnan, P.; Lin, R. T. P.; La, M.-V.; Chow, A. American Journal of Infection Control 2016, 44, 177.
(20) Saliba, V.; Washer, P.; Pett, P.; Kakkar, M.; Abbas, S.; Raghuvanshi, B.; McKee, M. J Public Health Pol 2016, 37, 1.
(21) Yong, D.; Toleman, M. A.; Giske, C. G.; Cho, H. S.; Sundman, K.; Lee, K.; Walsh, T. R. Antimicrobial Agents and Chemotherapy 2009, 53, 5046.
(22) Chen, Y.; Zhou, Z.; Jiang, Y.; Yu, Y. Journal of Antimicrobial Chemotherapy 2011, 66, 1255.
(23) Ho, P. L.; Lo, W. U.; Yeung, M. K.; Lin, C. H.; Chow, K. H.; Ang, I.; Tong, A. H. Y.; Bao, J. Y.-J.; Lok, S.; Lo, J. Y. C. PLoS ONE 2011, 6, e17989.
(24) Gupta, N.; Limbago, B. M.; Patel, J. B.; Kallen, A. J. Clinical Infectious Diseases 2011, 53, 60.
(25) Reading, C.; Cole, M. Antimicrobial Agents and Chemotherapy 1977, 11, 852.
(26) Ehmann, D. E.; Jahic, H.; Ross, P. L.; Gu, R.-F.; Hu, J.; Kern, G.; Walkup, G. K.; Fisher, S. L. Proceedings of the National Academy of Sciences 2012, 109, 11663.
(27) Gardiner, B. J.; Golan, Y. Expert Rev Anti Infect Ther 2016.
(28) King, A. M.; Reid-Yu, S. A.; Wang, W.; King, D. T.; De Pascale, G.; Strynadka, N. C.; Walsh, T. R.; Coombes, B. K.; Wright, G. D. Nature 2014, 510, 503.
(29) Brem, J.; van Berkel, S. S.; Aik, W.; Rydzik, A. M.; Avison, M. B.; Pettinati, I.; Umland, K.-D.; Kawamura, A.; Spencer, J.; Claridge, T. D. W.; McDonough, M. A.; Schofield, C. J. Nat Chem 2014, 6, 1084.
(30) Klingler, F.-M.; Wichelhaus, T. A.; Frank, D.; Cuesta-Bernal, J.; El-Delik, J.; Müller, H. F.; Sjuts, H.; Gittig, S.; Koenigs, A.; Pos, K. M.; Pogoryelov, D.; Proschak, E. Journal of Medicinal Chemistry 2015, 58, 3626.

What is claimed is:

1. A method to treat a bacterial infection from MBL producing bacteria in a subject, said method comprises administering to the subject: (a) an effective amount of a β-lactam antibiotic; and (b) an effective amount of a Bi(III) compound, or a pharmaceutically acceptable salt thereof, wherein the Bi(III) compound is a complex comprising Bi(III) coordinated to a ligand selected from L5 to L21:

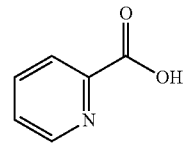

L5

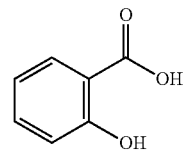

L6

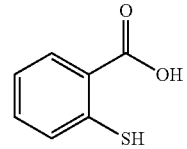

L7

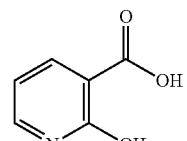

L8

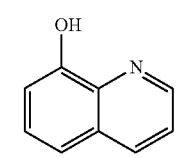

L9

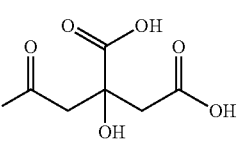

L10

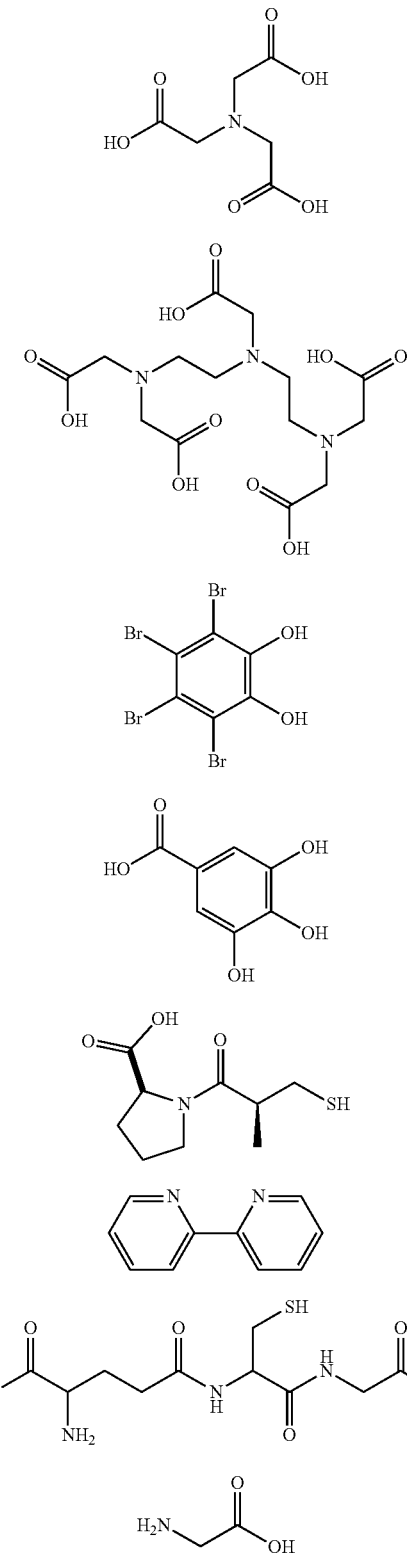

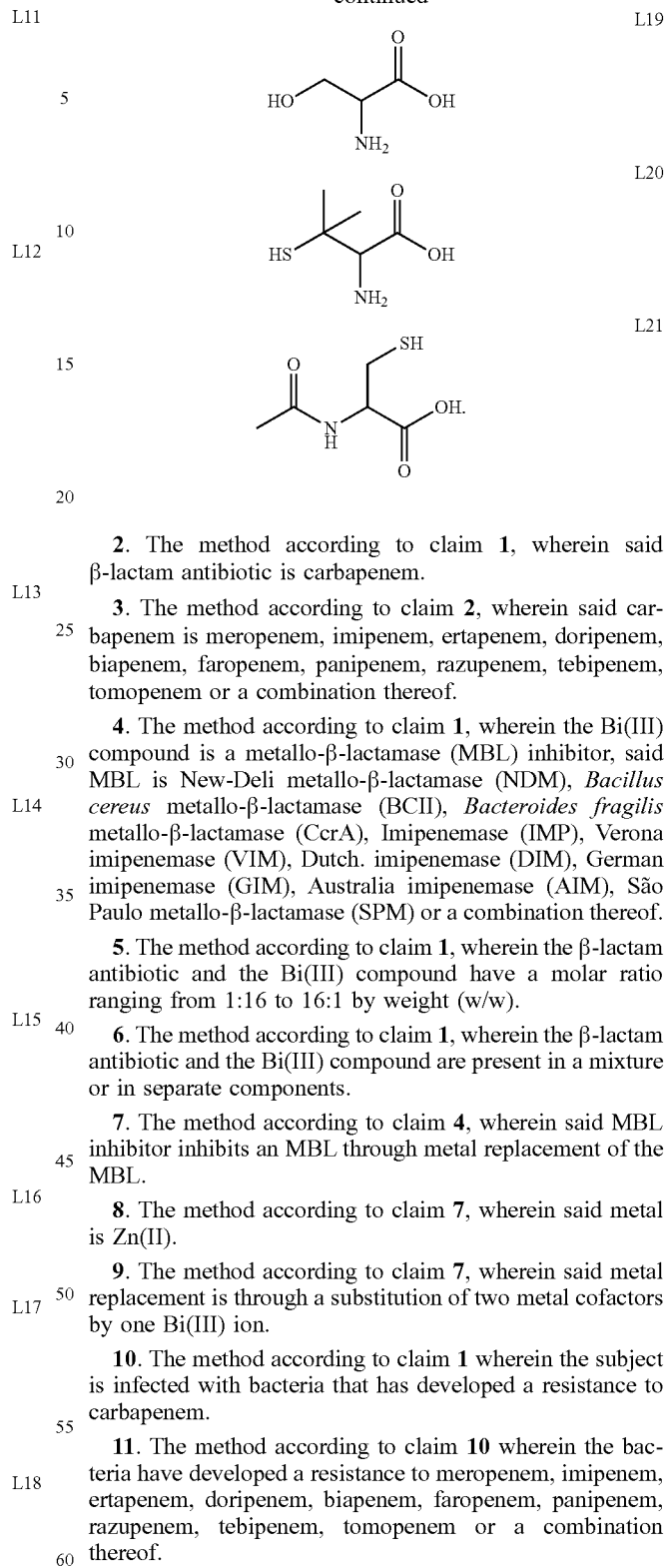

2. The method according to claim 1, wherein said β-lactam antibiotic is carbapenem.

3. The method according to claim 2, wherein said carbapenem is meropenem, imipenem, ertapenem, doripenem, biapenem, faropenem, panipenem, razupenem, tebipenem, tomopenem or a combination thereof.

4. The method according to claim 1, wherein the Bi(III) compound is a metallo-β-lactamase (MBL) inhibitor, said MBL is New-Deli metallo-β-lactamase (NDM), *Bacillus cereus* metallo-β-lactamase (BCII), *Bacteroides fragilis* metallo-β-lactamase (CcrA), Imipenemase (IMP), Verona imipenemase (VIM), Dutch. imipenemase (DIM), German imipenemase (GIM), Australia imipenemase (AIM), São Paulo metallo-β-lactamase (SPM) or a combination thereof.

5. The method according to claim 1, wherein the β-lactam antibiotic and the Bi(III) compound have a molar ratio ranging from 1:16 to 16:1 by weight (w/w).

6. The method according to claim 1, wherein the β-lactam antibiotic and the Bi(III) compound are present in a mixture or in separate components.

7. The method according to claim 4, wherein said MBL inhibitor inhibits an MBL through metal replacement of the MBL.

8. The method according to claim 7, wherein said metal is Zn(II).

9. The method according to claim 7, wherein said metal replacement is through a substitution of two metal cofactors by one Bi(III) ion.

10. The method according to claim 1 wherein the subject is infected with bacteria that has developed a resistance to carbapenem.

11. The method according to claim 10 wherein the bacteria have developed a resistance to meropenem, imipenem, ertapenem, doripenem, biapenem, faropenem, panipenem, razupenem, tebipenem, tomopenem or a combination thereof.

* * * * *